US012678556B2

(12) United States Patent
Sjölund et al.

(10) Patent No.: US 12,678,556 B2
(45) Date of Patent: Jul. 14, 2026

(54) MEDICATION FLUID DELIVERY DEVICE

(71) Applicant: LUNA HEALTH, INC., Wilmington, DE (US)

(72) Inventors: Per John Sjölund, San Diego, CA (US); Andre S. Gamelin, Vista, CA (US); Jack David Pryor, San Diego, CA (US); Cory McCluskey, Encinitas, CA (US); Steven Michael Teixeira, San Diego, CA (US); Sean Thomas Saint, San Diego, CA (US); Jasper Benke, San Diego, CA (US); Jon A Brilliant, Wilmington, DE (US)

(73) Assignee: Luna Health, Inc., Wilmington, DE (US)

( * ) Notice: Subject to any disclaimer, the term of this patent is extended or adjusted under 35 U.S.C. 154(b) by 593 days.

(21) Appl. No.: 18/142,788

(22) Filed: May 3, 2023

(65) Prior Publication Data

US 2023/0270933 A1     Aug. 31, 2023

Related U.S. Application Data

(63) Continuation of application No. PCT/IB2021/060206, filed on Nov. 4, 2021.

(Continued)

(51) Int. Cl.
*A61M 5/142*        (2006.01)
*A61M 5/14*         (2006.01)
(Continued)

(52) U.S. Cl.
CPC ........ *A61M 5/14248* (2013.01); *G16H 40/67* (2018.01); *A61M 2005/14252* (2013.01)

(58) Field of Classification Search
CPC .... A61M 5/14248; A61M 2005/14252; A61M 5/20; A61M 2005/1402;
(Continued)

(56) References Cited

U.S. PATENT DOCUMENTS 7,137,964 B2    11/2006 Flaherty
8,062,256 B2 *  11/2011 Carter ............... A61M 5/14248
                                                    604/151

(Continued)

FOREIGN PATENT DOCUMENTS

JP         2013516231 A      5/2013
WO        2015100248 A1      7/2015
(Continued)

OTHER PUBLICATIONS

The European Search Report for PCT application PCT/IB2021060206 dated Apr. 4, 2024.

(Continued)

*Primary Examiner* — Jason E Flick
(74) *Attorney, Agent, or Firm* — Veros Legal Solutions, LLP

(57)                    ABSTRACT

A medication fluid delivery device and methods are provided with the delivery device having a dispensing unit and a drive unit that are attachable together. The dispensing unit includes a dispenser for delivering medication fluid to a user and a reservoir configured to be filled with a variable amount of medication fluid received from a medication fluid injector. The drive unit includes a control unit that controls the drive unit and causes medication fluid in the reservoir to be pumped through the dispenser and includes a registration mechanism configured to act with the dispensing unit to determine a state the reservoir including an initial level of the filled reservoir.

29 Claims, 13 Drawing Sheets

Related U.S. Application Data

(60) Provisional application No. 63/110,258, filed on Nov. 5, 2020.

(51) Int. Cl.

| | |
| --- | --- |
| *A61M 5/168* | (2006.01) |
| *A61M 5/20* | (2006.01) |
| *A61M 5/31* | (2006.01) |
| *G16H 40/67* | (2018.01) |

(58) Field of Classification Search
CPC ........... A61M 2005/14268; A61M 2005/3114; A61M 2205/18; A61M 2209/045; A61M 5/1452; A61M 5/1684; A61M 2205/14; A61M 2205/3379; A61M 2205/3584; A61M 2205/8237; A61M 5/14244; A61M 2205/3569; A61M 5/1413; A61M 2005/1586; A61M 2205/3389; A61M 5/142; A61B 5/4839; A61B 5/6833; A61B 2560/0443; G16H 40/67; G16H 20/13; G16H 20/17; G16H 40/63
See application file for complete search history.

(56) References Cited

U.S. PATENT DOCUMENTS

| | | | |
| --- | --- | --- | --- |
| 8,147,446 | B2 | 4/2012 | Yodfat et al. |
| 8,465,460 | B2 | 6/2013 | Yodfat et al. |
| 8,556,866 | B2 | 10/2013 | Krulevitch et al. |
| 8,568,361 | B2 | 10/2013 | Yodfat et al. |
| 8,900,189 | B2 | 12/2014 | Yodfat et al. |
| 9,089,637 | B2 | 7/2015 | Chong et al. |
| 9,402,950 | B2 | 8/2016 | Dilanni et al. |
| 10,058,691 | B2 | 8/2018 | Yue et al. |
| 10,275,573 | B2 | 4/2019 | Mazlish et al. |
| 10,369,079 | B2 * | 8/2019 | Rodriguez ................ A61J 1/22 |
| 10,376,638 | B2 | 8/2019 | Levesque et al. |
| 10,420,883 | B2 | 9/2019 | Diianni et al. |
| 10,610,643 | B2 | 4/2020 | Mazlish et al. |
| 10,874,803 | B2 | 12/2020 | Cardinali et al. |
| 10,933,188 | B2 | 3/2021 | Gonnelli et al. |
| 10,987,468 | B2 | 4/2021 | Mazlish et al. |
| 11,083,852 | B2 | 8/2021 | Sjolund et al. |
| 11,116,899 | B2 | 9/2021 | Sjolund et al. |
| 11,229,741 | B2 | 1/2022 | Diianni et al. |
| 11,529,464 | B1 | 12/2022 | Pruijs et al. |
| 11,559,625 | B2 | 1/2023 | Kamen et al. |
| 11,684,714 | B2 | 6/2023 | Poetschke |
| 11,801,340 | B2 | 10/2023 | Antonio et al. |
| 12,088,137 | B2 | 9/2024 | Conrad et al. |
| 2011/0166544 | A1 | 7/2011 | Verhoef et al. |
| 2013/0267813 | A1 | 10/2013 | Pryor et al. |
| 2014/0324018 | A1 | 10/2014 | Bazargan et al. |
| 2016/0129178 | A1 | 5/2016 | Askarinya et al. |
| 2020/0170671 | A1 | 6/2020 | Schoonmaker et al. |
| 2021/0379282 | A1 | 12/2021 | O'Connor et al. |
| 2022/0211937 | A1 | 7/2022 | Kamen et al. |
| 2022/0211944 | A1 | 7/2022 | Mensinger et al. |
| 2022/0249773 | A1 | 8/2022 | Zheng et al. |
| 2022/0362469 | A1 | 11/2022 | Kim et al. |
| 2023/0211075 | A1 | 7/2023 | Fiechter et al. |
| 2024/0042128 | A1 | 2/2024 | Bang et al. |

FOREIGN PATENT DOCUMENTS

| | | |
| --- | --- | --- |
| WO | 2016181384 A2 | 11/2016 |
| WO | 2018218082 A1 | 11/2018 |
| WO | 2018229783 A1 | 12/2018 |
| WO | 2019089178 A1 | 5/2019 |
| WO | 2019118541 A1 | 6/2019 |

OTHER PUBLICATIONS

Corrected International Search Report and Written Opinion in International Patent Application No. PCT/IB2021/060206, mailed Jan. 26, 2022.

* cited by examiner

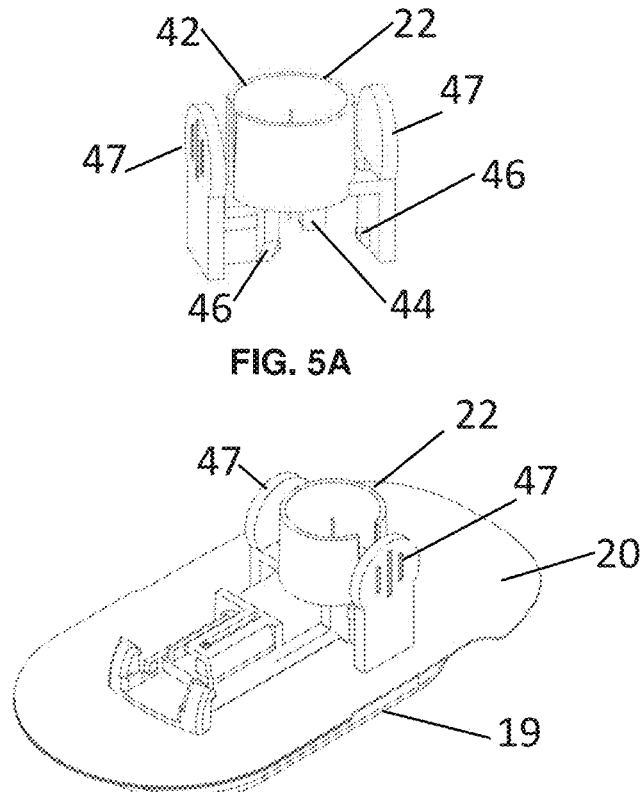
FIG. 5A
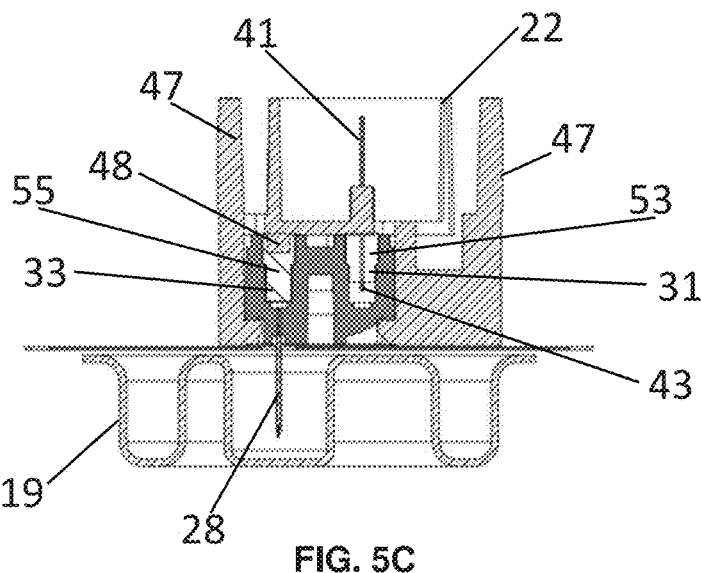
FIG. 5B
FIG. 5C

140

141

94

150

151

92

MEDICATION FLUID DELIVERY DEVICE

CROSS-REFERENCE TO RELATED APPLICATION

This application is a bypass continuation of International Application No. PCT/IB2021/060206 filed on Nov. 4, 2021, which claims priority from U.S. Provisional Patent Application No. 63/110,258, filed on Nov. 5, 2020, each of which is incorporated by reference, in its entirety, herein.

FIELD OF THE INVENTION

This disclosure relates to systems and methods for delivery of medication fluid to people or animals to treat or prevent disease.

BACKGROUND TO THE INVENTION

Medication fluids for the treatment or prevention of disease in human or animal bodies often need to be input into the body at intervals. Many different devices for medication fluid input are known including syringes, intravenous drips, cannulas, etc. Regular administration of medication fluids outside of a medical setting has a number of challenges to ensure safe and appropriate dosing.

One form of medication fluid that requires administration outside of a medical setting is insulin administration. Millions of insulin-dependent people with diabetes around the world rely on multiple daily injections (MDI) to control their diabetes. Insulin pens are the most common insulin delivery method globally. A majority of insulin is currently delivered by ordinary insulin pens as opposed to people that use alternative delivery methods like smart insulin pens, insulin pumps or automated insulin delivery systems.

People using insulin pens very often struggle to keep their blood glucose in a desired range overnight and may either have to wake up multiple times per night to administer insulin or risk hyper- and hypoglycemia. The result is disrupted sleep and other problems such as waking up tired, worried and groggy in the short term, and more profound health risks in the long term.

Automated Insulin Delivery (AID) systems such as an insulin pump with feedback from a continuous glucose monitor (CGM) can control blood glucose levels continuously, including overnight. These systems are expensive, may be highly intrusive, and may require frequent infusion set changes. Many insulin pen users either choose to, or do not have access to insulin pumps, and rely only on insulin pens. Switching between insulin pens during the day and insulin pumps overnight has not proved to be feasible. As a result people with diabetes may have no practical alternative to waking up to manually to modulate insulin at night with their insulin pen.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

According to an aspect of the technology there is provided a medication fluid delivery device comprising: a dispensing unit having a dispenser for delivering a medication fluid to a user and a reservoir configured to be filled with a variable amount of the medication fluid received from a medication fluid injector; and a drive unit attachable to the dispensing unit, the drive unit including a control unit that controls the drive unit and causes the medication fluid in the reservoir to be pumped through the dispenser; wherein the drive unit includes a registration mechanism configured to act with the dispensing unit to determine a state of the reservoir including an initial level of the medication fluid in the reservoir.

The dispensing unit may include a plunger moveable relative to the reservoir to apply a pressure to the medication fluid in the reservoir to pump it through the dispenser, and the drive unit includes a plunger operating member configured to engage with the plunger and to be driven by a drive mechanism.

The registration mechanism may include a sensor of the state of the reservoir, and wherein the state of the reservoir also includes one or more of the group of: that the reservoir is present, that the reservoir is engaged but not ready, a current level of the filled reservoir.

The registration mechanism may be integrated with the plunger operating member to detect a position of the plunger from which to determine a state of the reservoir. The registration mechanism may determine a position for an initially filled state of the reservoir by moving the plunger operating member in a direction opposite to a direction for dispensing the medication fluid. The registration mechanism may detect when the dispensing unit is attached to the drive unit. The registration mechanism may be used by the control unit to determine a volume of the medication fluid in the reservoir based on the position of the plunger operating member.

The registration mechanism may determine a home position of the plunger operating member as a reference for an empty state of the reservoir and an initial register position of the plunger operating member for a filled state of the reservoir.

The drive mechanism may include a stepper motor for controlling and measuring a linear movement of the plunger operating member and the control unit may control the amount of delivery of the medication fluid by activation of steps of the stepper motor.

The plunger operating member may be configured to activate a sensor of a detached state when the dispensing unit is detached from the drive unit and of an operational state when the plunger operating member is engaged with the plunger ready for delivery of the medication fluid.

The plunger operating member may be configured to have a first orientation depending on and indicating when the drive unit is detached from the dispensing unit and a second orientation engaged with the plunger and indicating an operational state. The plunger operating member may be configured to have a third orientation caused by the dispensing unit engaging with the drive unit and indicating a standby state ready for registering to result in the second orientation.

The control unit may be configured to automatically prime the plunger operating member by moving a predetermined priming distance in the plunger delivery direction to under-prime the medication fluid such that no medication fluid is delivered during the priming stage. The control unit may determine that the dispensing unit is attached to the drive unit and may control the plunger operating member to automatically prime the plunger operating member and to find an initial position. The control unit may be configured to reset the plunger operating member by moving the plunger operating member in the plunger delivery direction to a home position when it receives an indication that the drive unit is coupled to a charger unit.

The drive unit may include electrical contacts which connect to complementary electrical contacts of a recharging base station, so as to permit a power source to be recharged by the base station when the drive unit is disconnected from the dispensing unit.

The control unit may include a wireless communication module for communication with a remote device for receiving information used by a dosing algorithm of the control unit to control the delivery of the medication fluid from the dispensing unit.

The drive mechanism may include a stall detector to detect a motor stall due to an occlusion in the fluid delivery or a hard stop of movement of the plunger.

The control unit may be configured to initialize the plunger operating member by sensing that the dispensing unit is attached to the drive unit and controlling the drive mechanism to move in a first direction against the plunger delivery direction until the plunger operating member engages with an end of the plunger.

The control unit may be configured to generate status indications or alerts and transmit those indications or alerts to a user device and/or cause the indications or alerts to be displayed or indicated by the drive unit itself.

The reservoir may be configured to be filled from an auto-injector for automatically dispensing a pre-selected quantity of the medication fluid.

The medication fluid delivery device may include a coupler provided to releasably attach the dispensing unit to the medication fluid injector, wherein the coupler includes a first interface configured to couple to the injector and a second interface configured to couple to the dispensing unit, wherein the second interface includes a sealing arrangement configured to block a fluid path to the dispenser during filling of the reservoir.

The reservoir may include an inlet port configured to receive the medication fluid from the medication fluid injector and a second port configured to engage with the sealing arrangement. One of the first interface or the second interface may have a stronger attachment arrangement than the other of the first interface or second interface for staged decoupling of the coupler after filling. The coupler may provide a fluid passageway between the medication fluid injector and the reservoir and the coupler may be discardable once the medication fluid injector is used to fill the reservoir.

The dispensing unit may include a housing in which the reservoir is held, and a planar adhesive patch disposed on one side of the housing, and wherein the dispenser may be one or more needle or microneedle extending from an adhesive face of the adhesive patch opposite the housing, and wherein the planar adhesive patch includes a removal tab to aid removal from a user's skin.

The drive unit and the dispensing unit may be releasably attachable using a latch arrangement that is configured to disengage in a direction when a user holds the removal tab. The drive unit may be releasably attachable to the dispensing unit by means of complementary formations on the drive unit and on dispensing unit.

The dispensing unit may include a housing having an upstanding portion in which the reservoir and plunger are held including a rigid rib for engagement with a corresponding void of the drive unit for accurate positioning and movement of the plunger.

According to another aspect of the technology there is provided a method including: releasably attaching a medication fluid injector to a dispensing unit, the dispensing unit having a dispenser for delivering a medication fluid to the user and a reservoir for holding the medication fluid, actuating the medication fluid injector to fill the reservoir with a variable amount of the medication fluid from the medication fluid injector, detaching the medication fluid injector from the dispensing unit, attaching a drive unit to the dispensing unit, the drive unit including a control unit that controls the drive unit and causes the medication fluid in the reservoir to be pumped through the dispenser; and registering the drive unit with the dispensing unit to determine a state of the reservoir including an initial level of the medication fluid in the reservoir.

The method may include applying the dispensing unit to the user such that the dispenser engages the user to deliver the medication fluid to the user.

The step of attaching the medication fluid injector to the dispensing unit may include attaching the medication fluid injector to a coupler by means of a first interface of the coupler which connects to a needle attachment point of the medication fluid injector. The coupler may be provided pre-attached to the dispensing unit by means of the second interface, with the dispensing unit and coupler provided in a sterile package that is opened by the user.

The step of detaching the medication fluid injector from the dispensing unit may include: detaching one of the first and second interface of the coupler from the respective injector and dispensing unit; and detaching the other of the first or second interface of the coupler in a staged decoupling; and discarding the coupler.

The method may include: continuously using the delivery device through a period of constant application; intermittently through periods of application and non-application; or periodically through constant and or intermittent use over multiple wear sessions.

According to a further aspect of the technology there is provided a computer-implemented method for controlling delivery of a medication fluid to a user, the method carried out at a control unit of a medication fluid delivery device, wherein the medication fluid delivery device includes a dispensing unit having a dispenser for delivering the medication fluid to the user and a reservoir configured to be filled with a variable amount of the medication fluid received from an injector, and a drive unit associated with the dispensing unit that causes the medication fluid in the reservoir to be pumped through the dispenser, the method comprising: determining a state of the reservoir by registering the drive unit with the dispensing unit, wherein the state of the reservoir includes an initial level of the medication fluid in the reservoir.

The method may include receiving inputs from a registration mechanism to indicate different states of the reservoir. The method may include controlling the drive unit to deliver an amount of the medication fluid according to a dosing algorithm based on a monitoring of a requirement of the user. The method may include initializing the dosing algorithm to assume that a patient has a base level of the medication fluid and reducing the assumed amount over time.

The method may include: sensing that the dispensing unit is attached to the drive unit; and determining an amount in the reservoir from a position of a component of the drive unit in relation to the reservoir. The method may include: sensing that the dispensing unit is attached to the drive unit; and automatically priming the drive unit. The method may include: sensing that the dispensing unit is detached from the drive unit and the drive unit is coupled to a charging unit; and resetting the drive unit to a home position.

The method may include receiving wireless communication from a remote device including information used by the dosing algorithm of the control unit to control the delivery of the medication fluid from the dispensing unit. The information received from the remote device may include a type of medication to influence the behavior of medication delivery.

The method may include sending to the remote device information regarding the delivery of medication for the remote device to store and display. The information sent to the remote device may include one or more of the group of: dosing records, reservoir volume, and battery charge level.

In accordance with a further aspect of the technology there is provided a medication fluid delivery device comprising: a dispensing unit having a dispenser for delivering a medication fluid to a user and a reservoir for holding the medication fluid received from a medication fluid injector; a drive unit associated with the dispensing unit that causes the medication fluid in the reservoir to be pumped through the dispenser; and a coupler for engaging the medication fluid injector to the dispensing unit during filling of the reservoir, the coupler including a sealing arrangement configured to block a fluid path to the dispenser.

In accordance with a further aspect of the technology there is provided a medication fluid delivery device comprising: a dispensing unit having a dispenser for delivering a medication fluid to a user and a reservoir for holding the medication fluid received from a medication fluid injector, wherein the medication fluid is pumped from the reservoir through the dispenser by a plunger acting on the reservoir; and a drive unit associated with the dispensing unit including a plunger operating member that applies a force to the plunger during delivery of the medication fluid, wherein the plunger operating member is configured to move against a delivery direction of the plunger to locate at an initializing position against an end of the plunger.

In accordance with a further aspect of the technology there is provided a medication fluid delivery device comprising: a dispensing unit having a dispenser for delivering a medication fluid to a user and a reservoir for holding the medication fluid received from a medication fluid injector, wherein the medication fluid is pumped from the reservoir through the dispenser by a plunger acting on the reservoir; and a drive unit associated with the dispensing unit including a plunger operating member that applies a force to the plunger during delivery of the medication fluid, wherein the plunger operating member is configured to reset to a home position in a delivery direction of the plunger only when the drive unit is disconnected from the dispensing unit and attached to a charger unit.

In accordance with a further aspect of the technology there is provided a medication fluid delivery device comprising: a dispensing unit having a dispenser for a delivering medication fluid to a user and a reservoir for holding the medication fluid received from a medication fluid injector, wherein the medication fluid is pumped from the reservoir through the dispenser by a plunger acting on the reservoir; and a drive unit associated with the dispensing unit including a plunger operating member that applies a force to the plunger during delivery of the medication fluid, wherein the control unit is configured to automatically prime the drive unit by moving the plunger operating member a predetermined priming distance in a plunger delivery direction to under-prime the medication fluid such that no medication fluid is delivered during the priming stage.

In accordance with a further aspect of the technology there is provided a computer-implemented method for controlling delivery of a medication fluid to a user, the method carried out at a control unit of a medication fluid delivery device, wherein the medication fluid delivery device includes a dispensing unit having a dispenser for delivering a medication fluid to a user and a reservoir for holding the medication fluid received from the medication fluid injector, and a drive unit associated with the dispensing unit that causes the medication fluid in the reservoir to be pumped through the dispenser, the method comprising: controlling the drive unit to deliver an amount of the medication fluid according to a dosing algorithm with the dosing algorithm initialized to assume that a patient has a base level of the medication fluid and reducing the assumed amount over time.

In accordance with a further aspect of the technology there is provided an insulin delivery device comprising: a dispensing unit that is releasably attachable to an insulin pen, the dispensing unit having at least one needle for delivering insulin to a user and a reservoir for holding insulin received from the insulin pen, and a drive unit associated with the dispensing unit that causes insulin in the reservoir to be pumped through the at least one needle.

The dispensing unit may be releasably attachable to the insulin pen by means of a pen coupler. The pen coupler may include a first interface which connects to a needle attachment point of the insulin pen, and a second interface which connects to the dispensing unit.

According to a further aspect of the technology there is provided a method for delivering insulin to a user, the method including releasably attaching an insulin pen to a dispensing unit, the dispensing unit having at least one needle for delivering insulin to the user and a reservoir for holding insulin, actuating the insulin pen to fill the reservoir with insulin from the insulin pen, applying the dispensing unit to the user such that the at least one needle pierces skin of the user; detaching the insulin pen from the dispensing unit, and attaching a drive unit to the dispensing unit, the drive unit causing the insulin in the reservoir to be pumped through the at least one needle so as to deliver insulin to the user.

Embodiments of the invention will now be described, by way of examples only, with reference to the accompanying drawings.

BRIEF DESCRIPTION OF THE DRAWINGS

In the drawings:

FIGS. 5A to 5C are perspective views of a coupler of an example embodiment of a fluid medication delivery device;

US 12,678,556 B2

7

Figure 8:
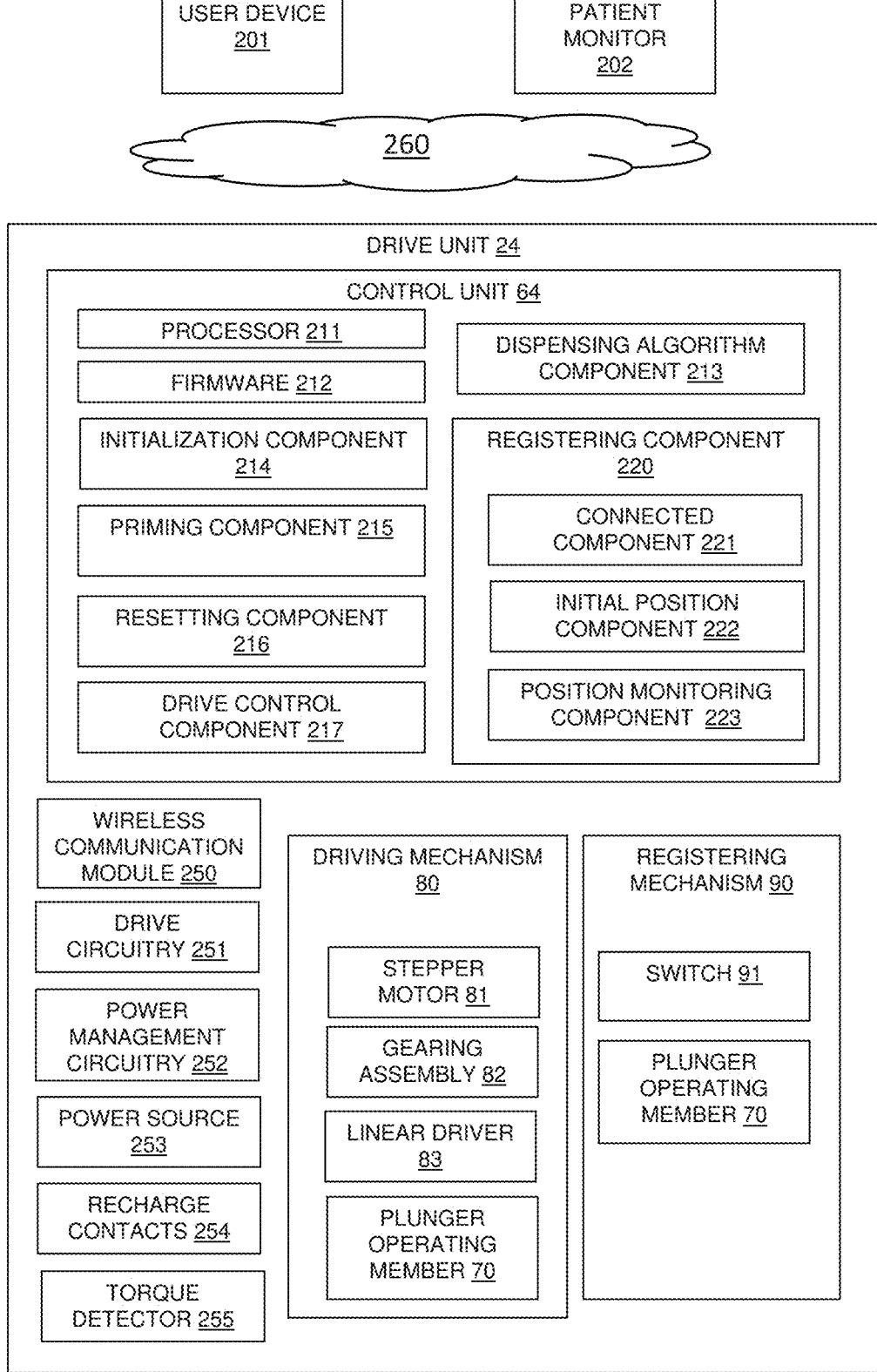
Figure 9:
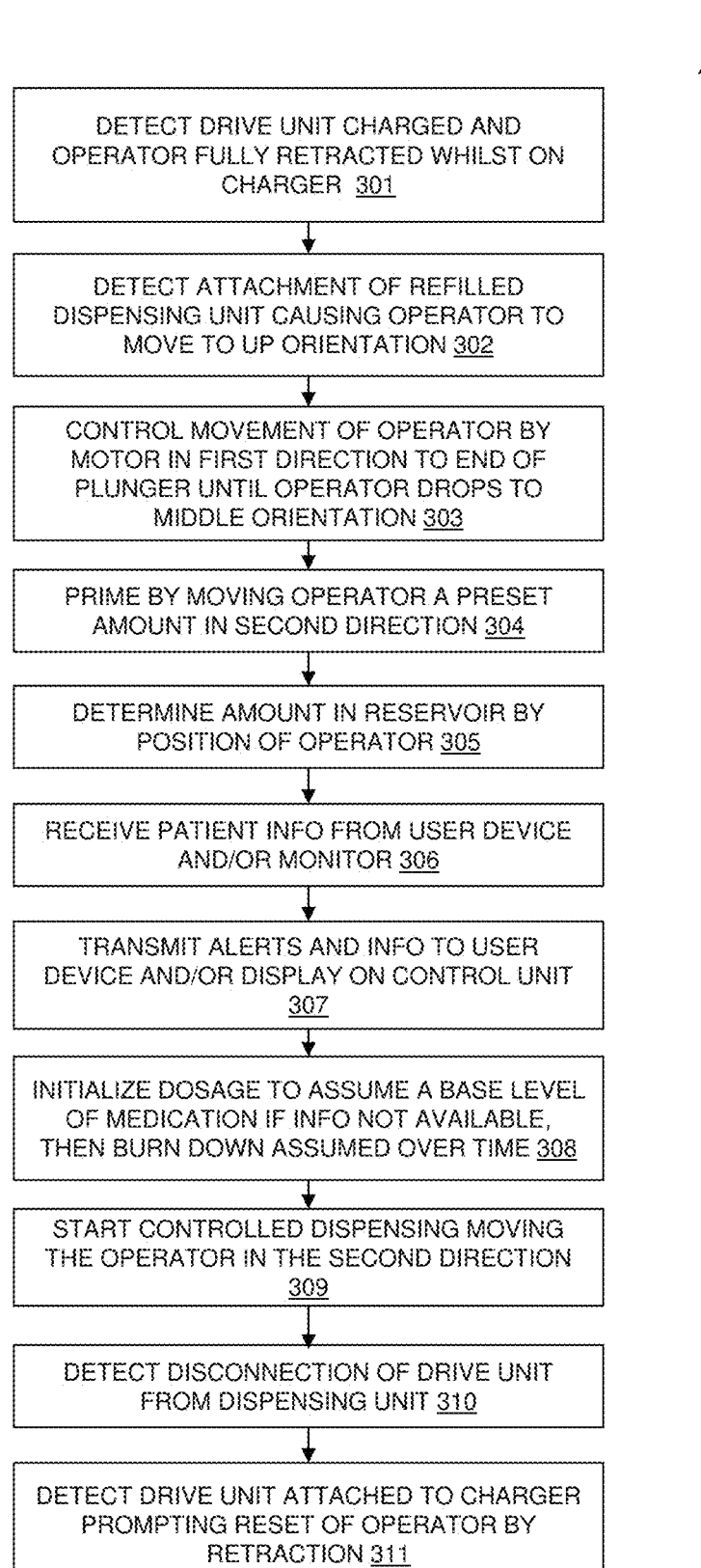
Figures 10A, 10B, 10C, 10D:
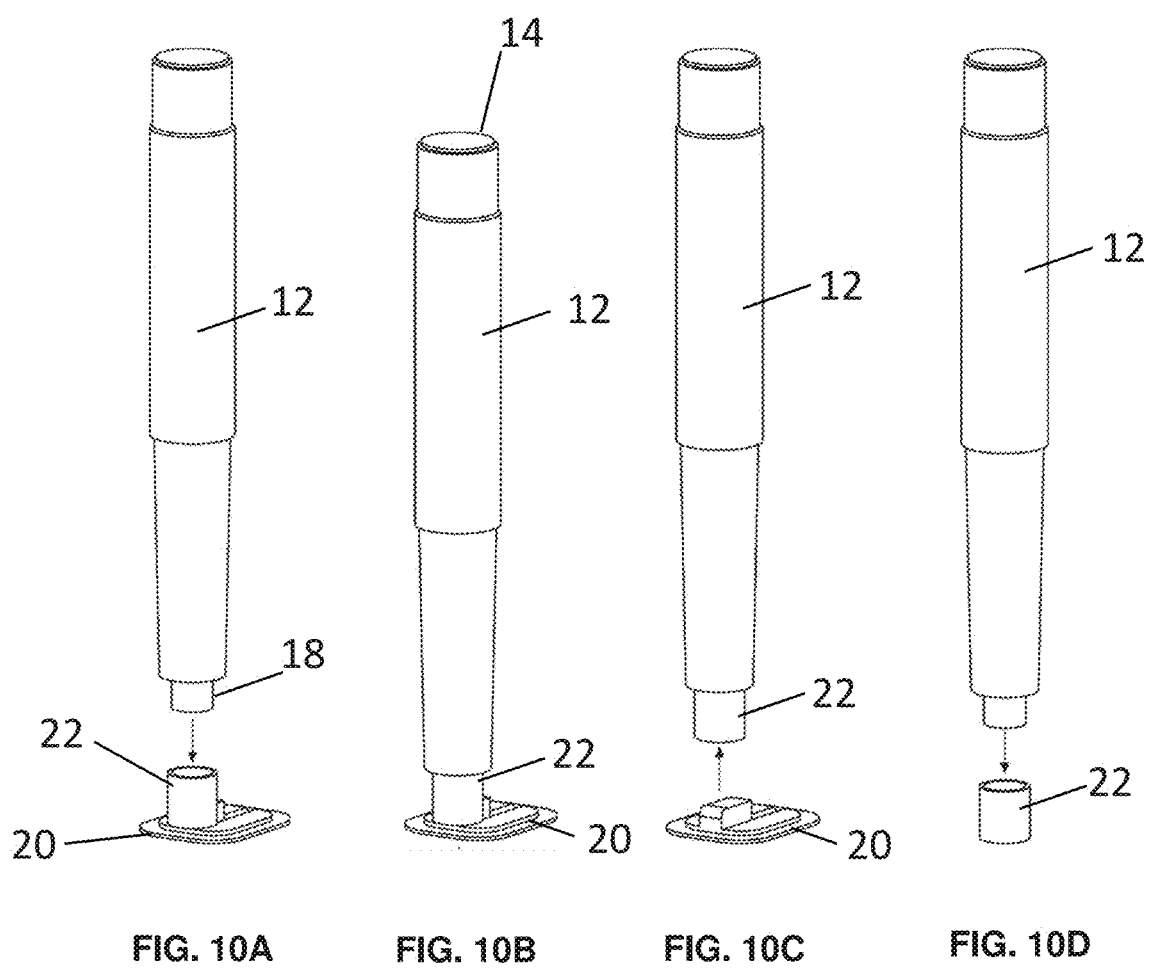
Figures 10E, 10F:
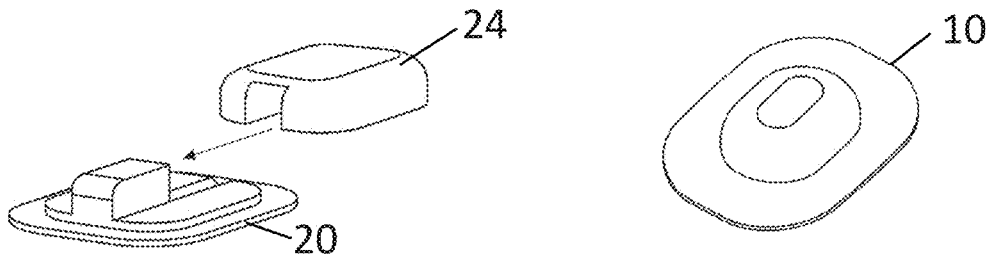
Figure 11:
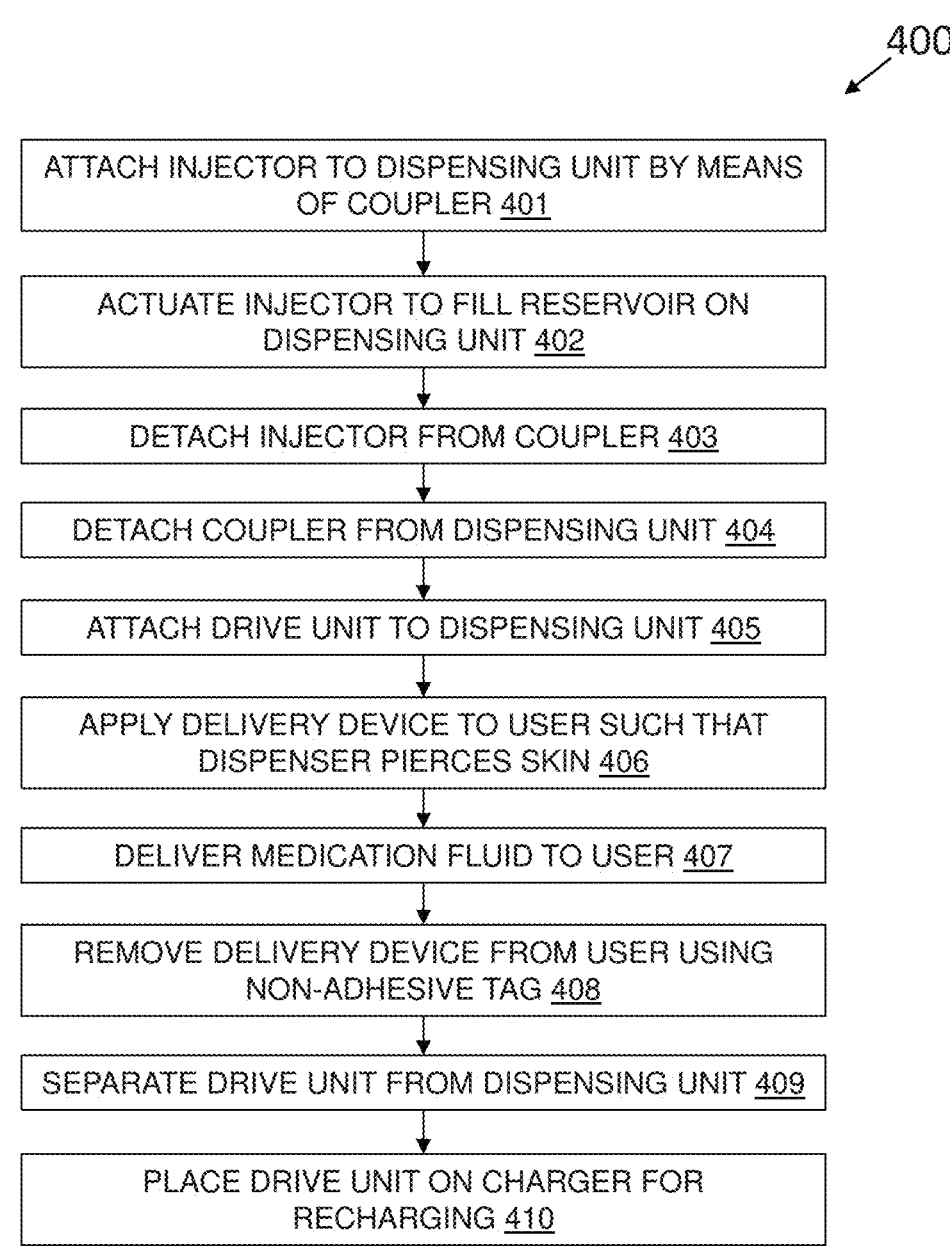

FIG. 8 is a block diagram showing a drive unit of an example embodiment of a fluid medication delivery device;

FIG. 9 is a flow diagram showing a method at a control unit of a drive unit of an example embodiment of a fluid medication delivery device;

FIGS. 10A to 10F shows a sequence of steps of a filling and assembly of an example embodiment of a fluid medication delivery device; and FIG. 11 is a flow diagram showing a sequence of steps of delivering a medication fluid using a fluid medication delivery device.

DETAILED DESCRIPTION WITH REFERENCE TO THE DRAWINGS

The disclosure provides devices, systems, and methods for delivering a medication fluid to a human or animal body. In embodiments of the disclosure, the medication fluid being dosed is insulin and an insulin delivery device is provided; however, the defined devices, systems, and method are applicable to other forms of medication fluid that require regular dosing.

The medication fluid delivery device is formed of two primary components: a dispensing unit that includes a fillable reservoir for the medication fluid and a dispenser for delivering the fluid percutaneously or subcutaneously; and a drive unit that includes a control unit for controlling a drive mechanism to cause the medication fluid to be delivered from the reservoir through the dispenser. In some embodiments, the dispensing unit is releasably attachable to the drive unit in a manner that allows interaction between the two primary components to control the delivery of the medication fluid from the reservoir through the dispenser. The drive unit may be a durable reusable component and the dispensing unit may be a disposable component. The combined dispensing unit and the drive unit are attachable to a user's body to deliver doses of the medication fluid over a time period, such as overnight, without user intervention. The dispenser of the dispensing unit may be at least one percutaneous or subcutaneous dosing element such as a needle or microneedle for delivering the medication fluid to a subject in need thereof.

Some of the aspects and features described herein may be applied in a single piece delivery device in which the dispensing unit and the drive unit are integrated, for example, as a fully disposable delivery device.

The drive unit includes a registration mechanism configured to act with the dispensing unit to determine a state of the reservoir. The registration mechanism determines an interaction between the drive unit and the dispensing unit to determine a state of the reservoir and provide an indication of the state to the control unit. The term "registration mechanism" is used as the drive unit "registers" with the dispensing unit. A state of the reservoir may include determining when the drive unit and dispensing unit are engaged together. A state of the reservoir may be when the reservoir is first engaged in the drive unit but the plunger not yet positioned. A state of the reservoir may be an initial level of the filled reservoir. The initial level of the reservoir may be dependent on the variable filling of the reservoir and may be in relation to a "home" or reset position. This initial level may be after an adjustment for a priming stage. A state of the reservoir may also extend to include a level in the reservoir during the dispensing process.

The registration mechanism may be used by the control unit to determine the volume of medication fluid in the reservoir and an amount of the medication fluid being delivered from the reservoir. The registration mechanism may be configured to register a position of the plunger engaged with the reservoir that relates to a volume level in the reservoir enabling the drive unit to interact accurately with the dispensing unit. The drive unit includes a control unit that acts with the registration mechanism to receive input regarding the state of the reservoir and to activate a drive mechanism. The drive mechanism may be used to determine the position of the plunger that relates to the volume level in the reservoir. The drive mechanism and the registration mechanism may be integrated by using a plunger operating member that acts against the reservoir plunger to determine the position of the plunger and to measure movement of the plunger. The control unit may include a priming stage and a resetting stage with corresponding control of the plunger operating member.

The fillable reservoir of the dispensing unit has an inlet port for coupling with a medication fluid injector allowing a user to input a selected variable amount of the medication fluid into the reservoir. The medication fluid injector may be a monitored source, allowing the control of the amount of medication fluid being administered from the medication fluid delivery device and other devices. The coupling may include the use of a disposable coupler providing a fluid passage between the injector and the inlet port. The injector may be an auto-injector for automatically dispensing a pre-selected quantity of medication fluid, such as an insulin pen.

The volume of the reservoir is determined by the process of finding the plunger position, counting a distance moved to find the plunger position, and translating the distance into a volume level of the reservoir. The distance may be counted by steps of a stepper motor and translating the step count to volume level. The translation from distance to volume may change along the reservoir, for example, due to a draft angle that assists in the molding process. Therefore, an equation or a look-up table is used determine the translation from steps to volume which is dependent on the location along the reservoir.

In an example embodiment, the medication fluid is insulin and the medication fluid injector is a portable auto-injector dosing device such as an insulin pen such that the medication fluid delivery device can be filled from the insulin pen allowing the total insulin being administered to be monitored as it is coming from the same source, i.e. the insulin pen. The medication fluid delivery device may be an automated insulin delivery (AID) device intended for nighttime delivery of insulin for people with diabetes that use insulin pens. The delivery device may be a precision insulin pump provided as a wearable patch. The delivery device includes a control unit that includes a dosing algorithm and receives glucose readings from a Continuous Glucose Monitor or user device and determines when insulin should be delivered.

Exemplary medication fluid delivery device, systems, and methods are now described in a non-limiting manner with reference to the figures. The embodiments shown in the figures are particularly applicable where insulin is the medication fluid.

FIGS. 1A to 1E illustrates a sequence of steps for filling and preparing the components of an example embodiment of a medication fluid delivery device (10) referred to as "a delivery device". An example of a delivery device is an insulin delivery device in the form of an automated insulin delivery (AID) device.

Figures 1A, 1B, 1C:
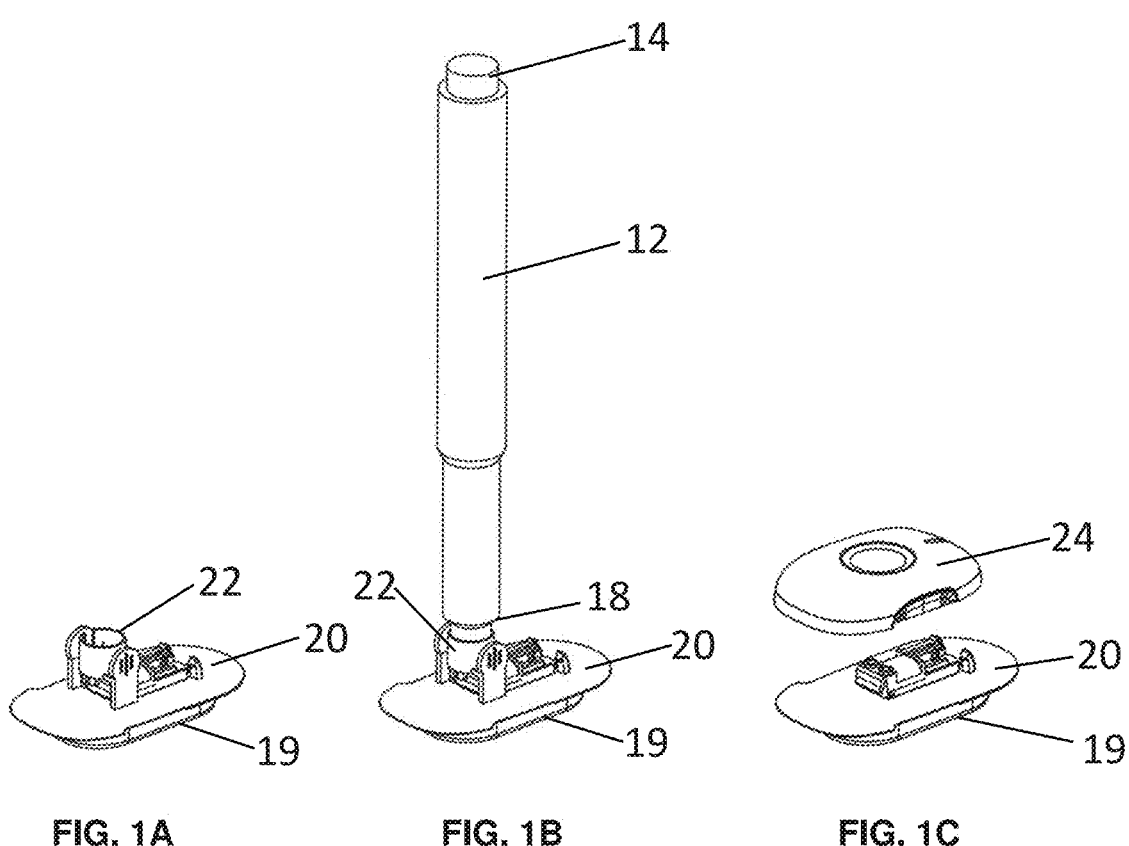
FIGS. 1A to 1E are a sequence of perspective views of preparation of an example embodiment of a fluid medication delivery device.

The delivery device (10) has two main components, a dispensing unit (20) and a drive unit (24). The drive unit (24)

is a reusable durable component that is used with multiple consumable dispensing units (20). The drive unit (24) may be used with hundreds of disposable dispensing units (20). The dispensing unit (20) may be provided with a coupler (22) as shown in FIG. 1A. The dispensing unit (20) may also be provided with a protective tray (19) to protect a dispenser on the underside of the dispensing unit (20) during the filling process.

A medication fluid injector (12) is attachable to the coupler (22) by engaging a tip of the injector (12) with the coupler (22) as shown in FIG. 1B. Alternatively, the injector (12) may engage directly with the dispensing unit (20) without the need for a coupler (22). The injector (12) may be a standard insulin pen which may have an injection button (14) with an associated dose selector (not shown), injector reservoir and a needle attachment point. The dispensing unit (20) may receive a variable amount of medication fluid from the injector (12) depending on the requirements of the user. The requirements may include, for example, the duration that the delivery device is intended to be used for or the dosage required by the user.

Figures 1D, 1E:
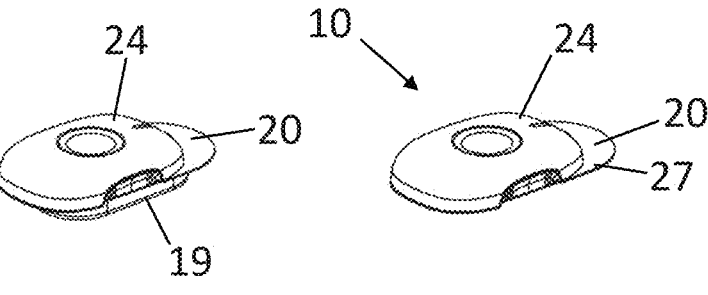

The drive unit (24) is attached to the filled dispensing unit (20) as shown in FIG. 1C to form the delivery device (10) that is still disposed in the protective tray (19) as shown in FIG. 1D. The delivery device (10) is removed from the protective tray (19) and adhered to the skin of the user in the form shown in FIG. 1E. In some embodiments, the dispensing unit (20) may be filled in situ on the user's skin before attaching the drive unit (24).

The dispensing unit (20) is capable of receiving the medication fluid from the injector (12) and percutaneously or subcutaneously delivering such medication fluid to a user, for example overnight while the user is asleep. The drive unit (24) may cause the medication fluid held in the dispensing unit (20) to be pumped through a dispenser extending from the dispensing unit (20).

Figure 2A:
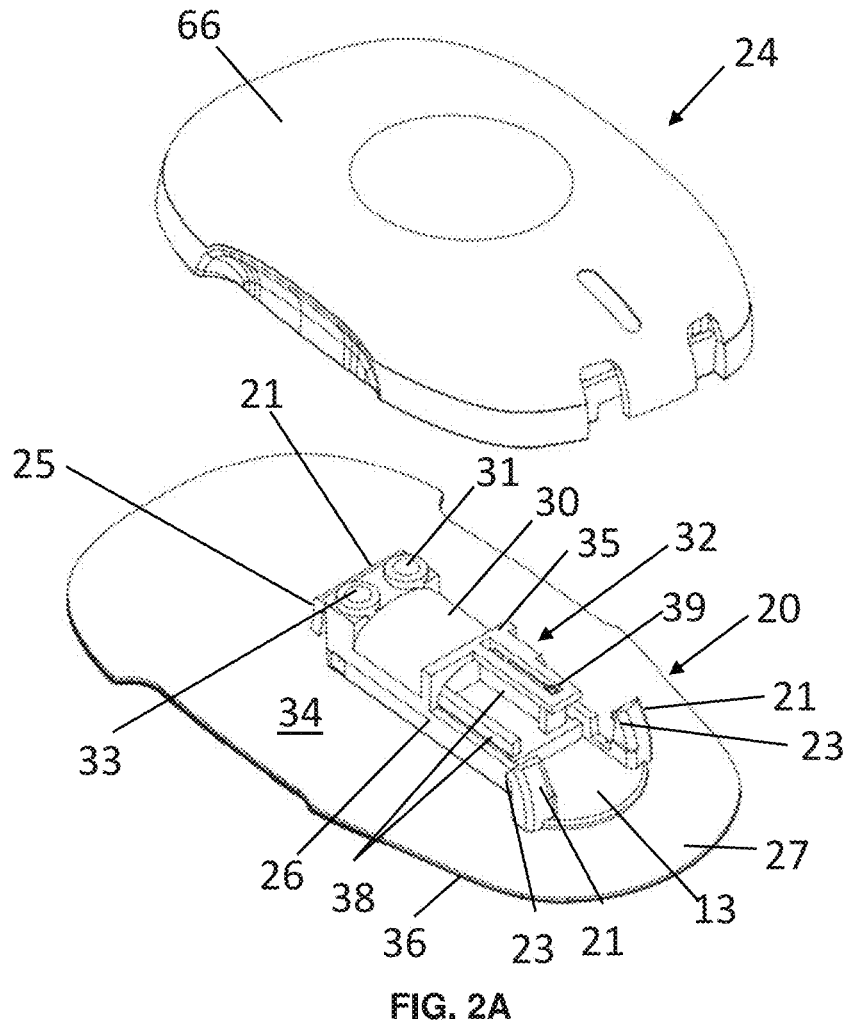
FIGS. 2A and 2B are perspective views of an example embodiment of a fluid medication delivery device including a dispensing unit and a drive unit.
Figure 2B:
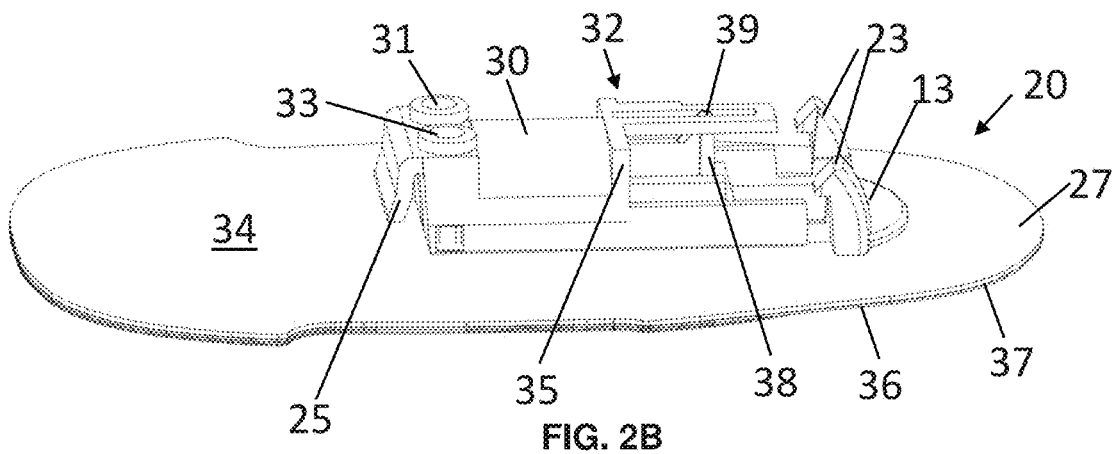

FIG. 2A shows an embodiment of the dispensing unit (20) and the drive unit (24) in more detail in a perspective view as they are to be attached together. FIG. 2B shows another view of the dispensing unit (20). The dispensing unit (20) may be a low cost single use sterile component that is fillable with the medication fluid and disposable after use in the delivery device (10).

The dispensing unit (20) includes a housing (26) that houses a reservoir (30) for holding the medication fluid received from the injector (12) until it is delivered through a dispenser (28) (shown in FIG. 3D), for example, in the form at least one needle or microneedle. The reservoir (30) may be fabricated from a translucent material to enable the user to verify that the reservoir (30) is filled correctly. The material of the reservoir (30) is compatible with the medication fluid and with irradiation sterilization processes. The reservoir (30) includes an inlet port (31) for coupling with the injector (12) directly or via the coupler (22) to receive the medication fluid into the reservoir (30) and an outlet port (33) providing an outlet to the dispenser (28), such as a needle. The input port (31) and the outlet port (33) may be formed by a dual septum that may be bonded to the reservoir (30), for example, by heat staking. The output port (33) may be configured to enable a plug to block the outlet port (33) during the filling process. The outlet port (33) may be bonded to the dispenser (28), for example, in the form of a needle or fine cannula.

The housing (26) may include an upstanding portion (32) in which the reservoir (30) is held. The upstanding portion (32) may be made from a suitable rigid material such as injection-molded plastic. A planar portion (34) may be disposed around the upstanding portion (32) with a flat face on an underside thereof and with a planar adhesive patch (36) disposed on the flat face of the planar portion (34). The planar portion (34) may be at least partially flexible to curve when adhering to a user's skin. The adhesive patch (36) may permit the dispensing unit (20) to be located on a user's skin for a duration of dosing. The adhesive patch (36) may adhere to a user's skin in a manner that it is secured until positively removed by pulling off the skin. The planar portion (34) may include a tab (27) that is devoid of adhesive. The tab (27) enables a user to remove the delivery device (10) easily from their skin by pulling on the tab (27). This is particularly useful with adhesive designed for longer term wear that may be harder to release. The tab (27) is configured to extend from one end of the dispensing unit (20) beyond the mated area of the drive unit (24) for ease of access as shown in FIG. 1E.

The dispenser (28) may be at least one needle or microneedles extending from the adhesive patch (36) opposite the upstanding portion (32). In some embodiments, the at least one needle may include an array of hollow microneedles. Microneedles can be made of several different materials including silicon, titanium, stainless steel and polymers. The at least one needle may also be an ordinary single steel needle, a Teflon infusion device, or the like. As an example, the needle may be a stainless steel hypodermic needle of 4-7 mm in length for percutaneous or subcutaneous application of the medication fluid.

The reservoir (30) may be in contact with a plunger (38) that acts against the reservoir (30). The plunger (38) is axially movable within the reservoir (30) located in the upstanding portion (32) so as to exert pressure on the insulin within the reservoir (30). The reservoir (30) may be a rigid chamber and the plunger (38) may have an attached o-ring seal that enables it to slide in relation to the rigid chamber. The rigidity of the chamber provides accuracy of dispensing so that positive displacement of the plunger (38) is directly proportional to fluid volume dispensed from the chamber.

In other embodiments, the plunger (38) may be formed of or integrated with an exposed portion of a wall of the reservoir (30). The reservoir (30) itself may be formed by a flexible bladder against which the plunger (38) acts to reduce the volume of the reservoir (30). In some embodiments, more than one bladder is within the reservoir, such as a cluster of bladders. The plunger (38) may move in a direction parallel to the plane of the planar portion (34) of the dispensing unit (20).

The plunger (38) is composed of a material that is compatible with the medication fluid and that can be sterilized by irradiation. The plunger (38) may have a shaft with an o-ring seal that provides a moving seal when engaging with the reservoir (30). The seal may be lubricated with a medication fluid compatible material. The plunger (38) is moveable in a first direction away from the reservoir (30) during filling of the reservoir (30) and is moveable in a second direction towards the reservoir (30) under the control of the drive unit (24) during the dosing process.

The plunger (38) may have two parallel elongate portions (38) that move together to exert a force on the reservoir (30) wall. The housing (26) includes a guiding member (39) in the form of a guide rail that engages with a projection of the plunger (38) with the guiding member (39) having an end stop to limit movement of the plunger (38) in the first direction during filling of the reservoir (30) to prevent over filling of the reservoir (30). The guiding member (39) may have a second end stop to limit movement of the plunger (38) in the second direction to indicate when the reservoir is empty or too low to dispense accurately. The guiding member (39) may act with one of the plunger elongate portions (38) whilst the other elongate portion (38) may interact with the plunger operating member (70) of the drive unit (24). The housing (26) may also include a stabilizing rib (35) disposed across the end of the reservoir (30) to prevent axial movement of the reservoir (30) when installed in the drive unit (24) to improve dose accuracy.

The housing (26) of the dispensing unit (20) includes engagement members (21) for engaging with the drive unit (24). The engagement members (21) retain the dispensing unit (20) in engagement with the drive unit (24) until the user intentionally separates them. The engagement members (21) are designed so that the drive unit (24) can be top loaded onto the dispensing unit (20) and separated from one end. In one embodiment as shown in FIG. 2A, the engagement members (21) are in the form of two latch arrangements (23, 25) on the dispensing unit (20) with a first latch arrangement (23) forming one or more downwardly extending and inwardly facing hook(s) at one end of the housing (26) and the second latch arrangement (25) forming one or more downward extending and outwardly facing hook(s) at the other end of the housing. A curved rigid portion (13) may extend beyond the first latch arrangement (23). This may be at the same end of the dispensing unit (20) as the non-adhesive tab (27) of the planar portion (34) provided for the user to remove the delivery device (10) from the body. The hooks may be molded with the housing (26) with no assembly required. Corresponding catch arrangements (29) are provided on the drive unit (24). In other embodiments, the engagement members (21) may include tongue-and-groove formations, sliding formations, locking formations, friction-fit formations or the like.

The planar adhesive patch (36) may be formed of a multilayer flexible material with a one day skin adhesive on one side and a more aggressive component adhesive on the other. The adhesive stackup may include a section (37) without adhesive that can be used as the tab (27) to assist in removal of the delivery device (10) from the user's skin. This can be accomplished by masking the adhesive in this area or by using a third material in the stackup that does not have adhesive.

Holding the section (37) when removing the device from the skin may also facilitate the movement of the tab (27) for separation of the dispensing unit (20) from the drive unit (24). The user peels the device off the skin in one direction with the flexible tab (27) and separates the drive unit (24) from the dispensing unit (20) by disengaging by a peeling motion in a direction away from the tab (27). This helps prevent unlatching while the delivery device (10) is worn since the body location prevents peeling in that direction. It also enables the user to peel the delivery device (10) off the body with the grip of one hand and, without changing that grip, to use the other hand to hold the drive unit (24) and peel it apart from the dispensing unit (20) in the other direction.

Gripping and peeling the drive unit (24) from the dispensing unit (20) may disengage the two latch arrangement (23, 25) of the engagement members (21) by pulling apart the first latch arrangements (23) from the catch arrangement (29) of the drive unit (24). The inwardly facing hooks of the first latch arrangement (23) may be configured to disengage when the rigid portion (13) is flexed in the direction opposite to the drive unit (24).

The adhesive patch (36) may also include release liners that can be removed during the manufacturing process to protect the integrity of the adhesives until it is assembled into the product. Alternatively, the adhesive patch (36)

release liner may be attached to the protective tray (19) (described further below), so that when the delivery device (10) is removed from the protective tray (19), the release liner is removed from the adhesive patch (36).

Figures 3A, 3B, 3C, 3D:
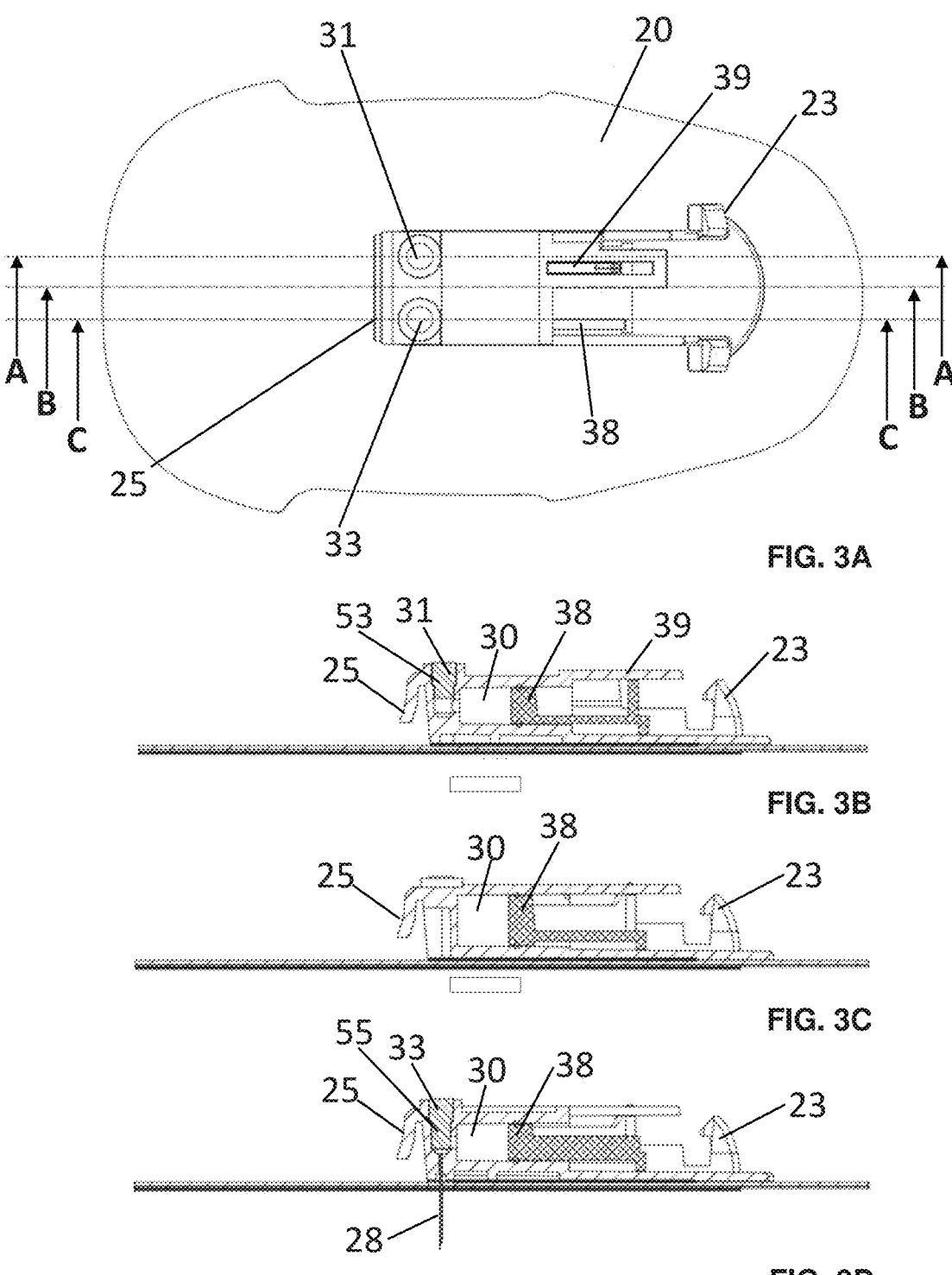
FIGS. 3A to 3D are a plan view and cross sections of a dispensing unit of an example embodiment of a fluid medication delivery device.

FIG. 3A shows a plan view of the dispensing unit (20) and FIGS. 3B, 3C and 3D show cross-sections through lines A-A, B-B and C-C of FIG. 3A respectively. The cross-section of FIG. 3B is through the inlet port (31) and shows the reservoir (30) and the elongate portion of the plunger (38) that engages with the guiding member (39). The inlet port (31) includes a septum (53) that is pierced by a needle of the coupler (22). The cross-section of FIG. 3C is through the center of the dispensing unit (20) and shows the reservoir (30) and plunger (38). This also shows the catch arrangements (23, 25) that engage with the drive unit (24). The cross-section of FIG. 3D is through the outlet port (33) showing the dispenser (28). The outlet port (33) includes a seal (55) that is pressed downward by a plug (48) of the coupler (22) to plug the fluid path to the dispenser (28) during filling (as shown in FIG. 5C).

Figure 4A:
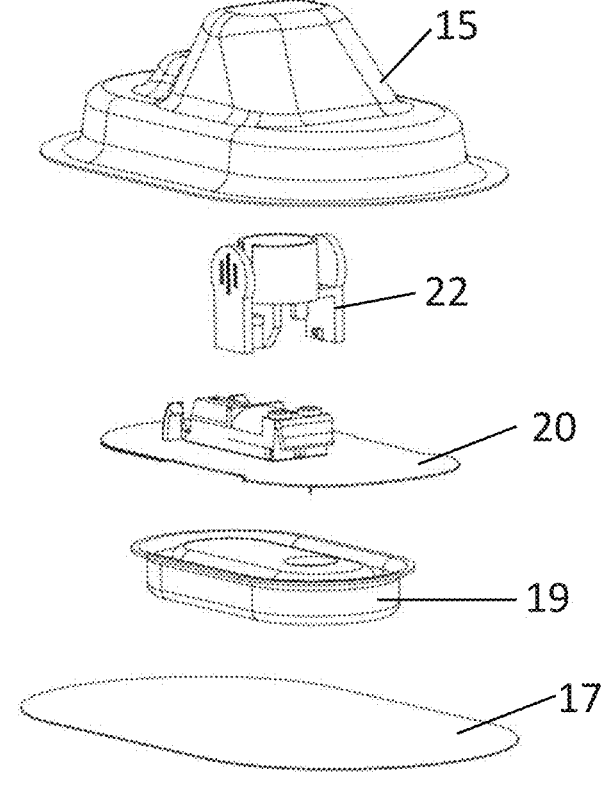
FIGS. 4A and 4B are perspective views of a packaged dispensing unit of an example embodiment of a fluid medication delivery device.
Figure 4B:
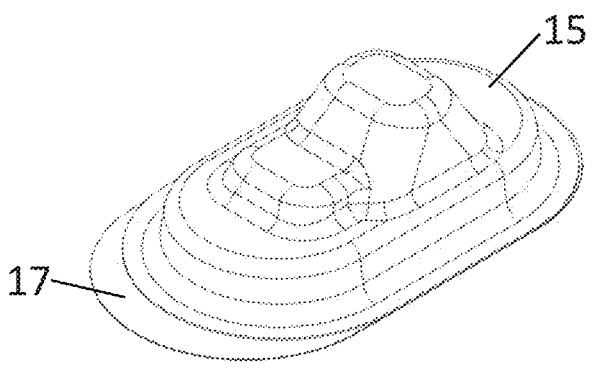

FIG. 4A shows an exploded view of the dispensing unit (20) and other components that may be packaged together as the disposable components. The components include the dispensing unit (20), the coupler (22), a protective tray (19), and a top and bottom packaging (15, 17). The protective tray (19) protects the dispenser (28) and supports it in place during the filling process. The top and bottom packaging (15, 17) may be in the form of a molded plastic tray and medical printed paper that can be sealed to provide a sterile barrier, or alternatively as a gusseted pouch with medical printed paper. FIG. 4B shows the sealed package before opening.

FIGS. 5A, 5B and 5C show a coupler (22) for use during filling of the reservoir (30) by an injector (12) such as an injector pen. The coupler (22) guides the injector (12) into the correct location and provides a fluid passageway between the injector (12). The dispensing unit (20) may be discarded once the injector (12) has been used to fill the reservoir (30) of the dispensing unit (20). The coupler (22) may be a generally cylindrical or tubular piece. The coupler (22) may include a first interface (42) which couples to a dispensing port (18) of the injector (12) at one end thereof (for example, the dispensing port may be a needle attachment point of a pen or syringe), and a second interface (44) which couples to the inlet port (31) of the dispensing unit (20) at an opposite end thereof.

The first interface (42) may include a releasable attachment mechanism that connects with the dispensing port (18) of the injector (12), for example, a screw coupling, a tongue-and-groove arrangement, a friction fit or the like. The first interface (42) may also include an internally disposed lance in the form of a needle, spike or blade for piercing a frangible seal of the dispensing port (18) of the injector (12) so that the medication fluid from the injector (12) can flow through the fluid passageway within the coupler (22).

The second interface (44) may include a releasable attachment mechanism by which the second interface (44) releasably connects to the dispensing unit (20), for example, such as a screw coupling, a tongue-and-groove arrangement, a friction fit or the like. In the illustrated embodiment, the second interface (44) is a latch arrangement (46) that retains the coupler (22) on the housing (26) of the dispensing unit (20) at the inlet port (31) with squeeze tabs (47) provided for unlatching. The second interface (44) may include a slot (45) of the coupler (22) configured to fit snugly over the upstanding portion (32) of the dispensing unit (20). As an alternative to the latching arrangement, squeezing a central portion of the cylindrical piece may cause the slotted end to open slightly, thereby enabling the coupler (22) to be removed from the dispensing unit (20) without a substantial pulling force being exerted thereon which could otherwise detach the adhesive patch (36) from its attachment. The second interface (44) may connect the fluid passageway to the inlet port (31) of the reservoir (30) on the upstanding portion (32). The inlet port (31) may have a non-return valve so as to prevent insulin from exiting the inlet port (31).

FIG. 5C is a cross section through the coupler (22) when attached to the dispensing unit (20) in the protective tray (19). The coupler (22) may have a double headed needle (41, 43) bonded into it. One needle (43) point pierces a septum of the inlet port (21) of the reservoir (30) and allows it to seal when removed and the other end (41) pierces a septum (53) on the injector (12) enabling the user to fill the reservoir (30) from the injector (12). The coupler (22) does not require threading it into place, instead there is a circular wall that guides the injector (12) onto the needle. The coupler (22) has a clip feature that allows it to be removed from the inlet port (31) of the reservoir (30) after the filling process.

The coupler (22) includes a molded plug feature (48) that presses down on a second septum or seal (55) of the reservoir (30) that leads to the outlet port (33) to the dispenser (28), thereby blocking the fluid outflow path during the filling process. This prevents the medication fluid from exiting the dispenser (28) during the filling process. When the reservoir (30) is filled, the plunger (38) is pushed back depending on the volume of the medication fluid that the user fills into the reservoir (30). This design enables the user to fill the reservoir (30) with a variable volume of medication fluid. As an example, the reservoir (30) is designed to be filled with up to 12 Units of insulin.

The coupler (22) interfaces (42, 44) may be configured such that the coupler (22) is more easily released from its connection to the reservoir (30) than from its connection to the injector (12) such that it remains attached to the injector (12) as the injector (12) is pulled away from the reservoir (30). The coupler (22) may be provided already attached to the dispensing unit (20). Alternatively, the coupler (22) may be more easily released from its connection to the injector (12) such that it remains in place on the reservoir (30) until removed. In both scenarios, a staged decoupling takes place.

The coupler (22) enables filling of the reservoir (30) directly from an injector (12) without additional needles. In one example, the injector (12) may be twisted into the coupler (22) and when it is untwisted, the coupler (22) is detached from the reservoir (30) with the injector (12). This is accomplished by having an interface that is stronger on the injector/coupler interface than the coupler/reservoir interface. Once the injector (12) together with the coupler (22) is detached from the reservoir (30), the coupler (22) can be removed from the injector (12) and discarded. Alternatively, the interface may be stronger on the coupler/reservoir interface and the injector (12) may be detached from the coupler (22) leaving the coupler (22) coupled to the reservoir (30) from where it may be removed and discarded.

The reservoir (30) is configured in manufacturing so that the plunger (38) is fully inserted into the reservoir (30). The user dials the desired number of units and inserts the injector (12) into the reservoir coupler (22). The needle in the coupler (22) pierces the septum on the injector (12) and enables the reservoir to be filled with medication fluid from the injector (12). The user dispenses medication fluid from the injector (12) into the reservoir (30) and the plunger (38) retracts as the reservoir (30) is filled with medication fluid.

This method minimizes air within the reservoir (30) and enables variable fill of the reservoir (30) by the user.

Figure 6A:
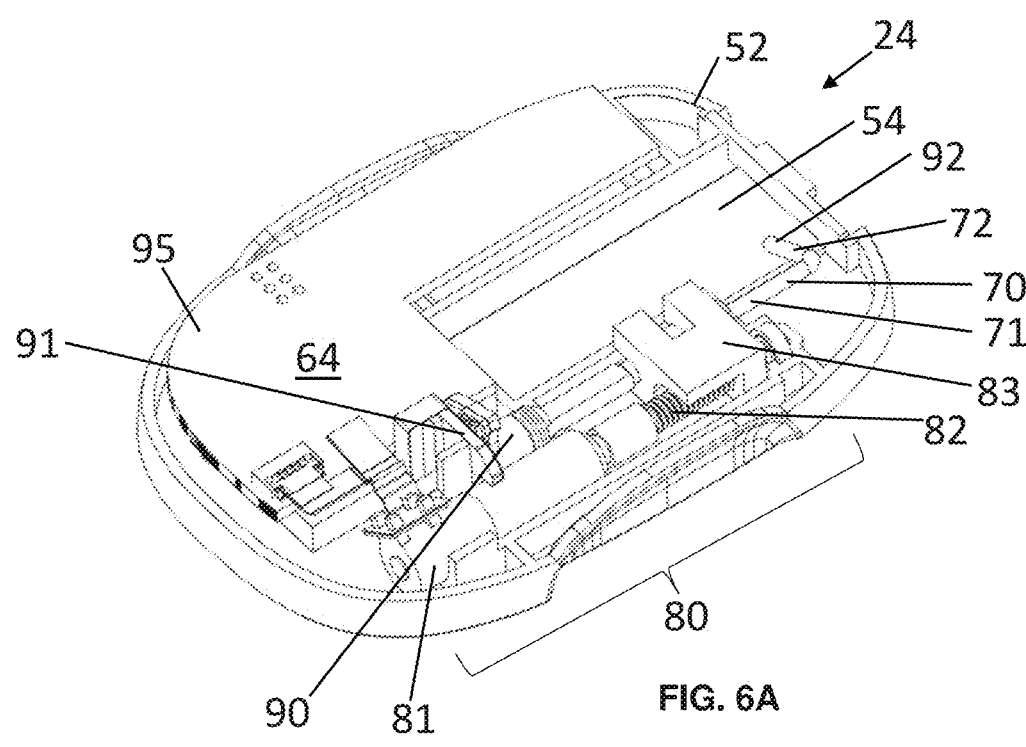
FIGS. 6A to 6D are perspective views of a drive unit of an example embodiment of a fluid medication delivery device.
Figure 6B:
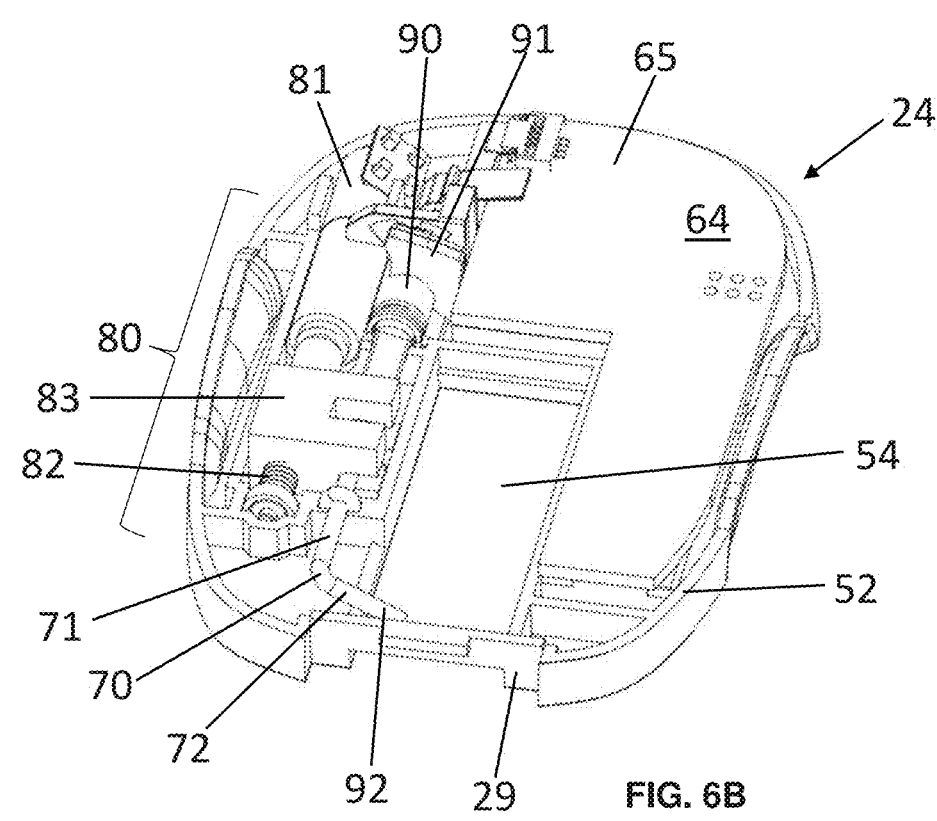
Figures 6C, 6D:
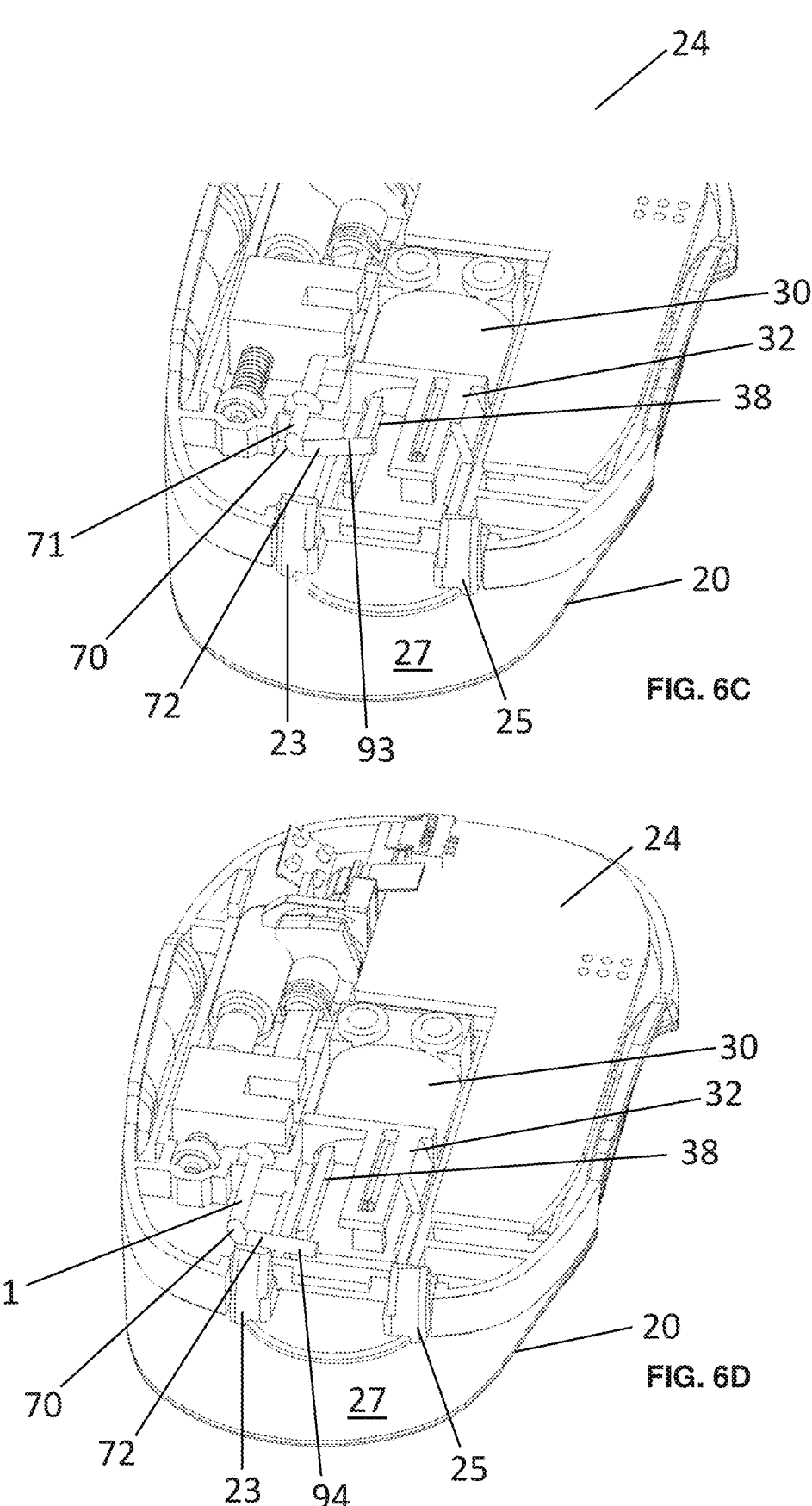

FIGS. 6A and 6B show the drive unit (24) from a top view with a cover removed and disengaged from a dispensing unit (20). FIGS. 6C and 6D show the drive unit (24) from a top view with a cover removed and engaged with a dispensing unit (20) that can be seen with the upstanding portion (32) of the housing (26), the reservoir (30) and the plunger (38) showing in a void (54) of the drive unit (24).

The drive unit (24) is associated with the dispensing unit (20) and capable of causing medication fluid in the reservoir (30) to be pumped out through the dispenser (28). The drive unit (24) is separably attachable to the dispensing unit (20), with the dispensing unit (20) being disposable while the drive unit (24) is reusable. The drive unit (24) may accordingly be attachable to successively used dispensing units (20), with the drive unit (24) being reusable and the dispensing units (20) being disposable after use.

The drive unit (24) may include a housing (52), the housing (52) including the void (54) into which the upstanding portion (32) of the dispensing unit (20), including the reservoir (30) and plunger (38), fits snugly when the dispensing unit (20) and drive unit (24) are attached together as shown in FIGS. 6C and 6D. The drive unit (24) may releasably attach to the dispensing unit (20) by means of complementary formations on the drive unit (24) to the engagement members (21) on the dispensing unit (20) as described and shown in FIG. 2A.

In the illustrated embodiment, outer surfaces of the dispensing unit (20) and the drive unit (24) when connected may provide a smooth outer surface with a flattened profile. For example, a combined height dimension of the dispensing unit and drive unit (24) may be less than 10 mm and preferably even less than 5 mm. A flattened profile enables the device to cause minimal disruption to a user while in use attached to a user's skin. In one example, the reservoir size may accommodate 120 microliters of medication fluid and for that size reservoir the volume range may be less than 20,000 mm$^3$ and preferably less than 10,000 mm$^3$. In a specific embodiment, the dimensions of the delivery unit (10) may be 47×32×8.7 mm (excluding the tab (27)) with a volume of approximately 13,000 mm$^3$.

The drive unit (24) may include a plunger operating member (70) capable of applying a force to the plunger (38) that moves to provide pressure on the reservoir (30) to dispense consistent increments of the medication fluid, for example, where the medication fluid is insulin, this may dispense in the range of 0.1 to 1.0 units at a time. The reservoir (30) and the plunger (38) of the dispensing unit (20) may align with the plunger operating member (70) when the dispensing unit (20) connects to the drive unit (24), such that the plunger operating member (70) moves linearly so as to apply a force to the plunger (38) and urge the insulin in the reservoir (30) out through the dispenser (28). It will be noted that in this embodiment the plunger (38) is disposed with an axis extending generally parallel to the planar portion, to permit the dispensing unit (20) to connect to the drive unit (24) by means of a sliding action generally parallel to the planar portion (34).

In the illustrated embodiment, the drive unit (24) includes an integrated drive mechanism (80) and registration mechanism (90). In other embodiments, the drive mechanism (80) and the registration mechanism (90) may be separate components. For example, the registration mechanism (90) may include a separate reservoir volume sensor or other mechanism to detect the reservoir volume when the drive unit (24) engages with the filled volume of the reservoir (30). The registration mechanism (90) determines the inter-relation of the drive unit (24) with the dispensing unit (20), specifically with the reservoir (30). The drive mechanism (80) operates the plunger (38) in relation to the reservoir (30).

This registration may include determining when the drive unit (24) and dispensing unit (20) are engaged together as well as determining an initial filled position of the reservoir in relation to a "home" or reset position and monitoring the level in the reservoir during the dispensing process.

The drive mechanism (80) and the registration mechanism (90) are connected to a control unit (64) including a micro-controller processor with firmware that controls the operation of the delivery device (10).

The drive mechanism (80) provides controlled movement of a plunger operating member (70) in the form of an arm (71) that moves linearly in the direction of the axis of the plunger (38) and the arm (71) having a transverse extension (72) that engages with the plunger (38). The arm (71) may be disposed linearly adjacent the reservoir (30) and plunger (38) for a compact arrangement. In the illustrated embodiment, the plunger operating member (70) is part of the registration mechanism (90) as it is used to determines the volume in the reservoir (30) as well as operating to dispense the medication fluid from the reservoir (30).

The plunger operating member (70) is driven by the drive mechanism (80) in the form of a stepper motor (81) in combination with a gearing assembly (82) and a linear drive mechanism (83) connected to the arm (71) of the plunger operating member (70).

The plunger operating member (70) provides input to the registration mechanism (90) that determines the status and registration of the reservoir (30) in relation to the drive unit (24). The registration mechanism (90) includes a rotatory switch (91) that is rotationally coupled to the arm (71) of the plunger operating member (70) such that the arm (71) can slide through as it translates.

The transverse extension (72) of the plunger operating member (70) has three orientations (92, 93, 94).

A down orientation (92) (shown in FIGS. 6A and 6B) occurs when the drive unit (24) is detached from the dispensing unit (20). The transverse extension (72) is biased into the down orientation (92) and is reset to a home position when in the down orientation (92). The home position is a retracted position corresponding to an empty reservoir and is used as a reference position. The plunger operating member (70) may be biased in the down orientation as a default orientation such that it returns to this orientation when the dispensing unit (20) is detached from the drive unit (24).

An up orientation (93) (shown in FIG. 6C) occurs when the drive unit (24) is first engaged with the dispensing unit (20) and the plunger (38) and reservoir (30) are inserted into the void (54) of the housing (52) of the drive unit (24). This causes the transverse extension (72) to be forced upwards such that it rests on the top of the plunger (38).

A middle orientation (94) (shown in FIG. 6D) occurs when the transverse extension (72) is moved to an end of the plunger (38) and drops down to engage the end surface of the plunger (38). This is an operational position ready to dispense the medication fluid by exerting a pressure on the plunger (38).

A sensor is provided in the form of a rotary switch (91) or other suitable sensor of the registration mechanism (90) that determines which orientation (92, 93, 94) the plunger operating member (70) is in and a signal is provided to the control unit (64). The registration mechanism (90) provides an indication of whether or not the dispensing unit (20) is attached to the drive unit (24). This is achieved by the rotary switch (91) sensing that the transverse extension (72) is in the down orientation (92).

The registration mechanism (90) acts with the drive mechanism (80) to determine an initial plunger (38) position referred to as an initial registered position. Once the dispensing has started, the registration mechanism (90) and the drive mechanism (80) may register how much of the medication fluid is in the reservoir at any time.

Referring to FIG. 7A to 7E, a sequence of figures shows the operation of the registration mechanism (90) and drive mechanism (80).

Figures 7A, 7B, 7C:
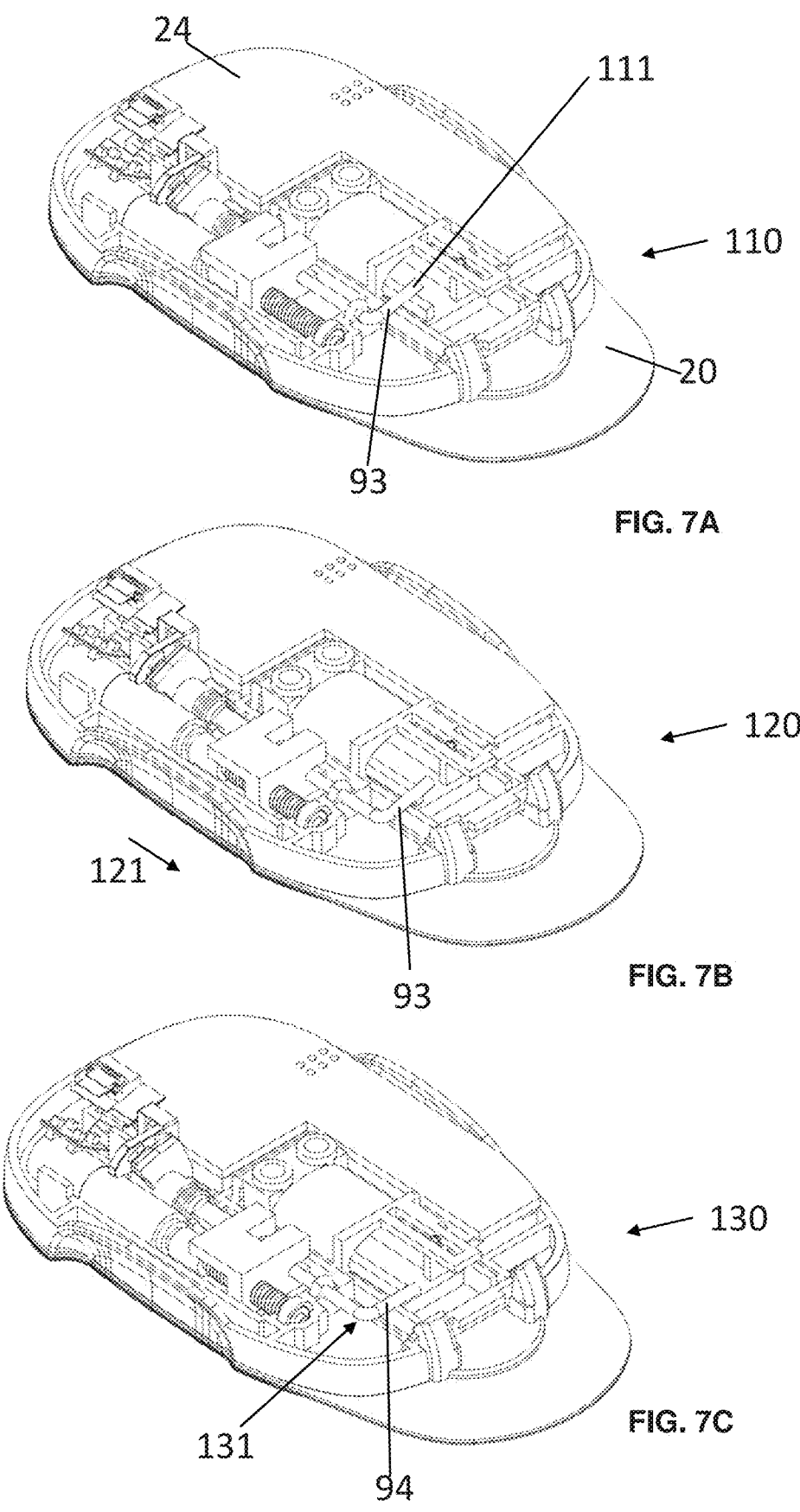
FIGS. 7A to 7E are perspective views of a drive unit of an example embodiment of a fluid medication delivery device showing a sequence of steps of the control unit.

FIG. 7A shows a first stage (110) when the dispensing unit (20) is first attached to the drive unit (24). The drive unit (24) is mated to dispensing unit (20) by pressing it straight down over the dispensing unit (20). When the drive unit (24) is mated to the dispensing unit (20), the plunger operating member (70) is rotated from the down orientation (92) to the up orientation (93) and is held up by the plunger (38). This indicates that the dispensing unit (20) has been connected, but the plunger (38) position has not yet been found. The transverse extension (72) of the plunger operating member (70) is pushed in an up orientation (93) by the plunger (38) as it is placed in the void (54) of the drive unit (24). The rotary switch (91) indicates this state to the control unit (64). The plunger operating member (70) will be in a fully retracted position at this stage as it will have been reset to a home position corresponding to an empty reservoir prior to the dispensing device (20) being attached. This resetting only takes place when the drive unit (24) is on a charger unit as this ensures that the dispensing unit (20) is not attached as resetting to the home position requires moving in the dispensing direction and this avoids any inadvertent dispensing if there is a control error.

FIGS. 7B and 7C show the next stages (120, 130) in which the transverse extension (72) of the plunger operating member (70) is moved by the drive mechanism (80) under the control of the control unit (64) in its up orientation (93). An initial registration to find the filled reservoir volume is achieved by the drive mechanism (80) moving the plunger operating member (70) in a direction (121) opposite to the dispensing direction. The device is designed so that the position of the plunger operator member (70) can be found by moving in the opposite direction to that which is required for fluid flow. If there is a position detection failure, the system will fail without dispensing any medication fluid into the user. This provides a safety feature of ensuring that no dispensing occurs during the initial registration process.

The registration mechanism (90) determines that the plunger operating member (70) in the up orientation (93) and uses the drive mechanism (80) to then drive the plunger operating member (70) in the direction (121) opposite to the plunger dispensing direction such that the transverse extension (72) of the plunger operating member (70) moves along the top of the plunger (38) until it reaches the end of the plunger (38) as shown in FIG. 7B. The transverse extension (72) of the plunger operating member (70) then drops down (131) to the middle orientation (93) as shown in FIG. 7C thereby registering the position of the end of the plunger (38). The middle orientation (94) is determined by the rotary switch (91) and also indicates to the control unit (64) that the drive unit (24) is now connected and the plunger operator member (70) is at the end of the plunger (38). The distance the transverse extension (72) of the plunger operating member (70) moves from the home position to the position at the end of the plunger (38) can be determined due to the distance of the movement of the plunger operating member (70). This distance is determined by the steps of the stepper motor (81) needed to move the plunger operating member (70) from the home position to the plunger position.

Figure 7D:
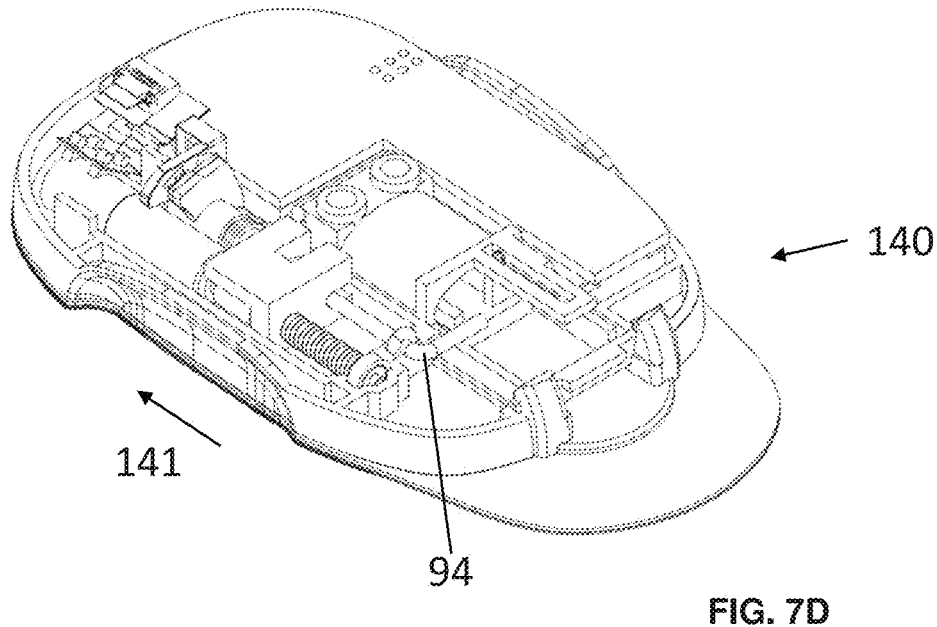

FIG. 7D shows a next operation stage (140). Once the plunger operating member (70) is in the middle orientation (94), this is detected by the rotary switch (91). The drive unit (24) is primed to expel air and remove slack in the system by moving a configured distance in the dispensing direction, as described further below. Once primed, the plunger operating member (70) is in an initial registered position at which an initial volume of the reservoir (30) can be calculated. The initial registered position can be determined from the distance moved in the first direction to find the plunger end, less the priming distance moved in the second position. The volume in the reservoir (30) can be calculated based on the distance taking into account a geometry of the reservoir (30).

The plunger operating member (70) is then controlled to dispense the medication fluid from the reservoir by exerting a pressure on the plunger (38) in a dispensing direction (141). The time and amount of the dispensing is controlled by the control unit (64). The position of the plunger operating member (70) is tracked by monitoring the step position from the home position. The amount of movement needed by the plunger operating member (70) to dispense a defined amount of the medication fluid is controlled by the control unit (64) by a number of steps of the stepper motor (81).

Figure 7E:
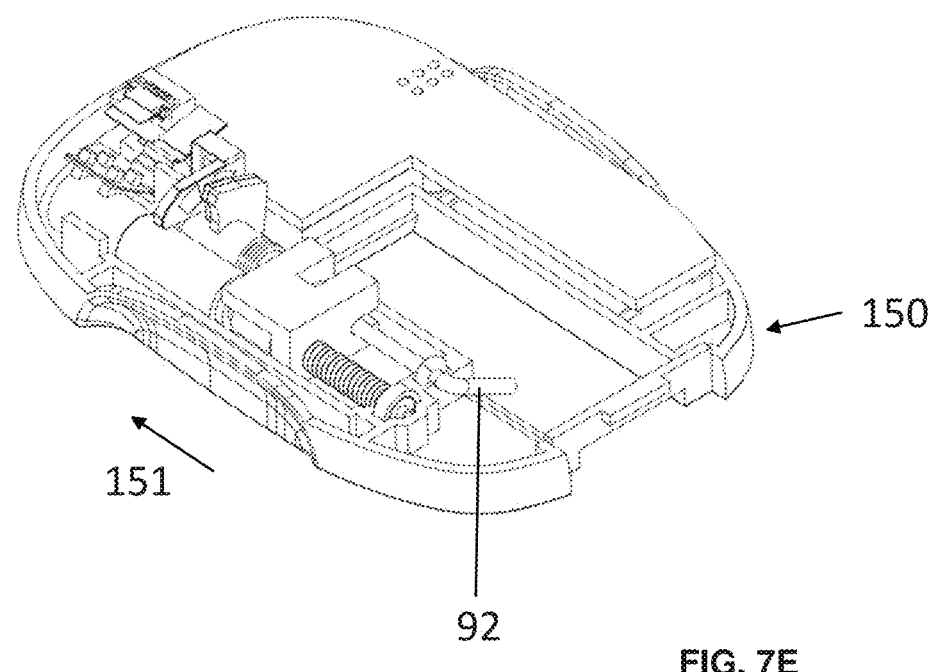

FIG. 7E shows a final stage (150) where the dispensing unit (20) has been removed from the drive unit (24) resulting in the transverse extension (72) of the plunger operating member (70) returning to its biased down orientation (92) which is detected by the rotary switch (91). In addition to the indication by the rotary switch (91) the control unit (64) senses when the drive unit (24) is attached to a charger to recharge its battery power source, and the control unit (64) resets the plunger operating member (70) to its home position retracted fully in the dispensing direction (151).

In an alternative embodiment for finding a position of the plunger with the filled reservoir, the plunger operating member may be moved by the drive mechanism to move the plunger using a drive current that is enough to move the plunger operating member on its own, but not enough to move the plunger operating member and the plunger together. Once the plunger operating member reaches the plunger, the motor will stall, and the control unit will detect the stall. If the motor is a stepper motor, this will result in a detectable voltage from the mismatch in the magnetic poles from the motor stall. This motor stall circuitry may be integrated into the stepper motor drive chip. The control unit may count the number of steps to the stall point which may be translated into a registered distance and filled volume of the reservoir. Once the initial registered position has been determined, the motor can be operated at full current to drive the plunger and dispense the fluid. The difference between the force required to move the plunger operating member and the force required to move the plunger operating member and the plunger together must be sufficient to distinguish the actions. A friction element may be required in order to accentuate the difference.

A further alternative embodiment may use a switch utilizing mechanical, optical, magnetic, inductive or capacitive technologies to determine a position of the plunger and a proximity of the plunger operating mechanism to the end of the plunger. The switch may be calibrated at the time of assembly by driving the mechanism into a hard stop and determining the number of steps between the switch trigger and the motor stall on the hard stop. This number can then be written into memory and used to improve the accuracy of the switch.

Once the plunger operating member (70) is registered with the end of the plunger (38), the control unit (64) may control the drive mechanism (80) to prime the delivery device (10) by moving a calibrated distance to move the plunger (38) in the dispensing direction. Slack in the device is due to finding the plunger position, compressibility of components, and air in the system. Priming may remove slack or air from the system and may account for compression losses before fluid is dispensed through the dispenser (28). The drive mechanism will move a fixed distance (number of steps) to take the slack out of the device. The priming number can be determined for the design by evaluating the number of steps required to prime the drive unit (24) or by individually measuring the number of steps required for each drive unit (24) and storing that value into the device during the manufacturing process.

The traditional method to prime a needle based system is to push until fluid is dispensed out of the needle. In order to ensure that no medication fluid is delivered during the priming process, the priming process under-primes the pump to account for tolerances to ensure that no insulin is dispensed. An additional step of the priming process may occur on the first delivery of the medication fluid, by taking up the remainder of slack based on empirical testing and tolerance analysis. Due to the small amount of air being provided in the described dispensing unit and the percutaneous or subcutaneous application, under-priming is possible. The under-priming is therefore designed to expel as much air as possible without dispensing any medication fluid. The control unit (64) may determine the distance to be moved by the plunger (38) (for example, as a number of steps of the stepper motor) required for this process based on empirical testing and tolerance analysis. Calculating the number of steps for priming and the first delivery ensures that the delivery device (10) is accurate as priming will mostly occur on the body. Priming may take some time to complete and the user may have already applied the delivery device (10) to their skin during this time, therefore, under-priming is a safety feature to ensure no medication fluid is delivered to the user during the priming.

The control unit (64) may take into consideration the geometry of the reservoir (30) when determining a distance to be moved by the plunger (38) (for example, as a number of steps of the stepper motor) required to dispense a defined volume. For example, if the reservoir (30) is tapered or has a draft angle from molding, the step count may be increased as the reservoir (30) tapers more narrowly requiring a greater linear movement to dispense a unit of the fluid. The translation of distance to volume may be determined by using an equation or a look-up table to determine the translation from distance to volume which is dependent on the location along the reservoir.

The movement of the plunger operating member (70) is monitored by the control unit (64) during dispensing and to determine when this is nearing exhaustion. This may be carried out by determining the number of steps moved by the stepper motor (81) to monitor the amount of volume in the reservoir (30).

The drive mechanism (80) may also include a stall detection mechanism (83) that detects a motor stall of the motor (81) that indicates an occlusion or the hard stop of the plunger (38) movement. The control unit (64) may interpret from the monitored reservoir volume, if the motor stall is due to the hard stop or an occlusion and may provide appropriate alerts.

The control unit (64) works with the stepper motor (81) by generating step pulses and direction signals for the stepper motor (81). The stepper motor (81) is an electromagnetic device that converts digital pulses into mechanical shaft rotation that is translated into a linear movement by the gearing assembly (82) and linear drive mechanism (83).

The drive mechanism (80) may include a telescoping linear drive mechanism (83), such as a screw drive, which may be driven by a gearing assembly (82) which in turn is driven by the stepper motor (81). The stepper motor (81) may be powered by a power source that may include a battery (62), for example a rechargeable battery. The drive unit (24) may also include electrical contacts (not shown) which connect to complementary electrical contacts of a recharging base station (not shown), so as to permit the battery (62) to be recharged by the base station when the drive unit (24) is disconnected from the dispensing unit (20).

A further safety feature may be provided that the plunger operating member (70) is only reset to its home position which is a fully retracted position corresponding to an empty reservoir (30) when the drive unit (24) is on charge. Inadvertent resetting by movement to the fully retracted position of the plunger operating member (70) when the drive unit (24) is still attached to the dispensing unit (20) runs the risk of dispensing fluid to the user. Therefore, a safety feature is provided to ensure that the resetting is only possible once the drive unit (24) is on the charger.

In the illustrated embodiment, the drive unit (24) is a modular unit that includes the drive mechanism (80), a power source and a control unit (64). The control unit (64) may be housed immediately beneath a cover (66) (shown in FIG. 2A) of the drive unit (24) in a generally shallow compartment therein, and may include a printed circuit board with control electronics and a communications antenna (not shown). The control electronics could include power electronics, wireless communications electronics, a processor, and optionally an encryption microprocessor, a temperature sensor and an occlusion sensor circuit.

Referring to FIG. 8, a block diagram shows an example embodiment of the drive unit (24). The drive unit (24) includes the control unit (64) and a wireless communication module (250) for communication via a wireless network (260) with a user device (201) such as a mobile phone, laptop or desktop computer and/or for communication with a patient monitor (202) such as a continuous glucose monitor (GCM). The control unit (64) may determine, by means of information received from the patient monitor (202) or from the user device (201), when to dose the medication fluid to the user. The control unit (64) may also be configured to generate status indications or alerts and transmit those indications/alerts to the user device (201) and/or cause the indications/alerts to be displayed or indicated by the drive unit (24) itself, for example, by way of flashing lights, sounds and/or haptic feedback.

The control unit (64) includes a microcontroller in the form of a processor (211) with firmware (212) that controls the operation of the drive unit (24). The firmware (212) is provided by many of the components of the control unit (64). The processor (211) may be a hardware module or a circuit for executing the functions of the described components which may be software units executing on the at least one processor (211). Memory may be configured to provide computer instructions to the processor (211) to carry out the functionality of the components.

The control unit (64) includes a registering component (220) for registering the drive unit (24) with an attached dispensing unit (20). The registering component (220) includes a connected component (221) to detect when the dispensing unit (20) is attached to the drive unit (24). The registering component (220) includes an initial position component (222) for detecting an initial filled position of the reservoir and plunger of the dispensing unit (20) in relation to the drive unit (24). The registering component (220) includes a position monitoring component (223) for detecting a position of the plunger of the dispensing unit (20) during the dispensing operation.

The registering component (220) may determine a volume of medication fluid in the reservoir based on the position of the plunger as determined by the registering mechanism (90) using the plunger operating member (70). The rotary switch (91) (or other status indictor or sensor) of the registering mechanism (90) may provide indications of the plunger state and position to the registering component (220). The registration component (220) may base its volume determination on the dimensions and geometry of the reservoir to translate linear movement of the plunger to fluid volume.

The control unit (64) includes a dispensing algorithm component (213) that may be in communication with the user device (201) and/or the patient monitor (202) and determines when to dispense a dose by means of the dispensing unit (20). In the example of the medication fluid being insulin, the dispensing algorithm component (213) determines when to provide a dose and calculates insulin on board the user.

The control unit (64) includes a drive control component (217) for controlling the driving mechanism (80) according to the dispensing algorithm component (213). This may control the driving mechanism (80) to operate the stepper motor (81) to move the plunger operating member (70) via the gearing assembly (82) and the linear drive mechanism (83). The drive control component (217) may also operate under the control of the registering component (220) to find the initial registered position by driving the driving mechanism (80) against the dispensing direction.

The control unit (64) includes an initialization component (214) for initializing the dispensing algorithm component (213) to assume that a patient has a base level of the medication fluid and reducing the assumed amount over time.

The control unit (64) includes a priming component (215) to work with the drive control component (217) to prime the dispensing unit (20) by moving the plunger a calibrated distance without dispensing any of the medication fluid. The priming component (215) may be calibrated during manufacturing of the device.

The control unit (64) includes a resetting component (216) for resetting the plunger operating member (70) when it is determined that the dispensing unit (20) is no longer attached to the drive unit (24). This includes receiving a signal from recharging contacts (254) of the drive unit (24) that are used to recharge the power source (253) from an external source. The resetting component (216) may work with the drive control component (217) to move the plunger to a home position in a fully retracted position.

The drive unit (24) also includes drive circuitry (251) and power management circuitry (252) that may be disposed on a same printed circuit board as the control unit (64). The power management circuitry (252) may include a power monitor, boost converter and power on reset control circuitry located on the printed circuit board. The drive unit (24) may include a steel plate so the charger can utilize magnets to hold the drive unit (24) in place during charging.

The drive unit (24) also includes a stall detector (255) to enable stall detection which is used for occlusion detection and end of travel detection. This may provide a signal to the control unit (64).

The stepper motor (81) and gearing assembly (82) provide an accurate measure of distance and the linear drive mechanism (83) may be a lead screw drive that translates the stepper motor rotary drive to a linear motion. The control of the driving mechanism (80) uses a sequence that reduces the possibility of inadvertent operation. An alternative embodiment may use a direct current motor.

As the motor and lead screw are elongate, the reservoir (30) and driving mechanism (80) are provided side by side. This is accomplished by providing the plunger operating member (70) on the end of the lead screw and retracting the lead screw in order to push the medication fluid out of the reservoir (30). The plunger operating member (70) is designed to contact the plunger and push the plunger to drive the medication fluid out of the reservoir as the stepper motor (81) is advanced. The plunger operating member (70) rotates in order to enable position sensing and connection sensing.

The power source (253) may be a lithium rechargeable battery, such as a lithium polymer (LIPO) batter with a small capacity (10-20 mAh) and high discharge rate (10 C). As most of the power is dissipated during short periods of time when the motor needs to be moved, the battery needs to either be oversized for one night use or have a high discharge rate.

The rotary switch (91) provides a three position sensor (disconnected, connected, connected/end of pusher) that combines the operation of two sensors into one mechanism. This detects when the drive unit (24) is connected to the dispensing unit (20) and also the position of the plunger operating member (70) during operation.

A charger unit may be provided, for example, a table top lithium battery charger that aligns the drive unit (24) and holds it in electrical contact while it charges. Features of the charger unit include spring loaded charging pins and magnets to provide a retention force to hold the drive unit (24) against the charging pins. The charger unit may have a weighted bottom and/or bumpers to grip a surface so that the charger does not slip off a table. The charger unit may include a USB connector to plug into a wall charger or computer (alternatively user replaceable batteries could be used for charging). The charger unit may indicate when charging is in process (i.e. flashing LED) and when it is charged to greater than a certain percentage (i.e. solid LED when greater than 80% charged). An 80% charge level is deemed to be sufficient to run the device and charging to this level will occur quickly since this is generally in constant current mode for a lithium battery. Charging above 80% typically works in a constant voltage mode that charges slower.

Referring to FIG. 9, a flow diagram (300) shows an example embodiment of the method carried out by the control unit (64) of the delivery device (10).

The method may detect (301) that the drive unit is charged with the plunger operating member (referred to as the operator in the figure) fully retracted to a home position having been reset whilst on charge. This may be detected by a sensor (such as the rotary switch (91)) of the registration mechanism.

The method may detect (302) the attachment of a refilled dispensing unit to the drive unit (24). This is detected by the sensor as the dispensing unit causing the operator to move to an up orientation as the reservoir and plunger are inserted into the void of the drive unit. The method may control (303) movement of the operator by the motor in a first direction opposite to the dispensing direction of the operator until the operator drops to a middle orientation at the end of the plunger. Once the dispensing unit (20) is attached to the drive unit (24), the device may be applied to the user's skin.

The method may prime (304) the delivery device by moving the operator a preset distance in a second direction that is the dispensing direction. The distance moved is calibrated to take up the slack in the device without dispensing any of the medication fluid. The method may determine (305) the volume in the reservoir at an initial registered position based on the distance the motor moves the operator from the home position to the initial registered position against the direction of the delivery taking into account the priming distance. Priming (304) and finding the initial registered position (305) may be carried out once the delivery device is attached to the user's skin.

The method may receive (306) patient information from a user device and/or a patient monitor during the method and may incorporate the received information into a dosing algorithm. The method may transmit (307) alerts and information to the user device and/or display alerts on the control unit. Receiving (306) and transmitting (307) information may occur prior to and throughout the dosing session.

The method may initialize (308) a dosage to assume a base level of medication in the patient (such as an insulin on board amount) and apply a burn down of the medication level over time. The method may start the controlled dispensing (309) of the medication fluid in accordance with a dosing algorithm moving the operator in the second direction by distances determined based on the required volume of a dose.

The method may detect (310) a disconnection of the drive unit from the dispensing unit and may detect (311) that the drive unit is attached to a charging unit prompting the resetting of the operator to retract it in the second direction to the home position.

The dosing algorithm is provided in the control unit (64). In the case of insulin, this is a correction bolus algorithm that is run when new glucose readings are available (typically these are provided every 5 minutes by the CGM). The dosing algorithm computes Insulin On Board (IOB) (based on a decay model over time) and calculates the user's insulin sensitivity based on user provided information of long acting insulin use. This information is used to calculate the required amount of insulin to provide to the user. If insulin information is available, then the starting IOB can be calculated and used in the algorithm. If no information is available, the algorithm will assume that the starting IOB is corresponding to the glucose reading in which case no insulin is required. As time goes on, the IOB will decay and the control system will correct for any differences between the glucose readings and IOB.

The distance the plunger (38) is pushed (number of steps) on the first dose will be larger than nominal to account for the under-priming. The number of added steps will be determined by testing a sample size that is statistically significant.

The distance the plunger (38) is pushed on subsequent doses (number of steps) can be variable to account for a draft angle on the reservoir. Manufacturing of some molded components requires a draft angle to properly release the component from the mold. This draft angle could be in the range of 0-½%, which over the length of the chamber could amount to an error of up to +/−5% if it is left uncompensated.

The control unit (64) knows the position of the plunger operating member (70) and the approximate end of travel for the plunger (38). On the last dose, the control unit (64) can either stop at a known position or drive the plunger (38) until it reaches a hard stop by monitoring the motor for a stall event. The control unit (64) monitors the number of steps and translates this into the dose size for the last dose. Since it is preferable to make use of all the medication fluid that is available, the last dose may be whatever medication fluid is left in the reservoir (30) which will be less than the nominal dose size.

The wearable dispensing device (10) is removed from the body once the session is complete and the drive unit (24) is separated from the dispensing unit (20). The control unit (64) will know once this is done and the control unit (64) resets the mechanism to the home position. However, this movement is in the direction of fluid flow, so if there is a sensing failure, this could cause the contents of the reservoir (30) to be dispensed. A preferred method is to reset the registration and drive mechanism once the drive unit (24) is placed on the charger unit since it is not possible for the system to dispense fluid into the user while the drive unit (24) is on the charger unit.

Once the drive unit (24) is placed on the charger unit, the registration and drive mechanism can be retracted to the home position. The drive unit (24) may use the step count from this home position for all distance measuring and may use stall detection on the stepper motor to detect hard stops (like a limit switch) in case there is an error in the step count. This eliminates the need for an encoder to detect position.

The drive unit's (24) lithium battery may be charged by placing it on the charger unit where the pins make contact with the charger unit. This process may take a few hours to complete. The charger unit may indicate when the battery is being charged and when it is sufficiently charged for use.

FIGS. 10A to 10F show a sequence of figures for preparing the dispensing device (10) and FIG. 11 illustrates a flow diagram (400) of a method of delivering a medication fluid to a user using the delivery device (10). As illustrated in FIG. 10A, the dispensing unit (20) may be pre-packaged together with the coupler (22) already attached to it and included in a sterile package (not shown). Once removed from the sterile package, the injector (12) is then releasably attached (401) to the dispensing unit (20) by means of the first interface (42) of the coupler (22) which connects to a dispensing port (18) of the injector (12). The lance within the first interface (42) pierces a frangible seal of the dispensing port (18), for example, at a needle attachment point, of the injector (12) to permit the medication fluid to move from the injector (12) to the dispensing unit (20). In one embodiment, the medication fluid is insulin and the injector (12) is an insulin pen.

Referring to FIG. 10B, the user dials a variable amount of medication fluid (for example, in the case of insulin, most likely less than 12 units) on their injector (12) and actuates (402) the injector (12) so as to inject the medication fluid directly into the reservoir (30) of the dispensing unit (20) by pressing the injection button (14) on the insulin pen (12), so as to fill the reservoir (30).

In one embodiment, the user then applies (403) the adhesive patch (36) of the dispensing unit (20) onto the user's skin where it can be used to dose insulin percutaneously or subcutaneously. The injector (12) may be used to apply the dispensing unit (20) to the user's skin before attaching the drive unit (24) to the dispensing unit (20). The injector (12) may securely hold the dispensing unit (20) in place and to exert force against the skin so as to cause the dispenser (28) (such as at least one needle) to pierce the user's skin and result in a firm attachment of the adhesive patch (36). In an alternative embodiment, the user applies (403) the fully assembled dispensing unit (10) as shown in FIG. 10F to the user's skin by hand.

FIG. 100 illustrates a next stage where the injector (12) with the coupler (22) attached is withdrawn, detaching the injector (12) from the dispensing unit (20) by detaching the coupler's (22) second interface (44) from the dispensing unit (20). To assist in the de-coupling, the user may squeeze a central portion of the coupler (22) so as to open the slot (54) thereon as previously described or to release an attachment means. A next stage shown at FIG. 10D is to detach the coupler (22) from the injector (12) by detaching the first interface (42) of the pen coupler (22) from the dispensing port (18) of the injector (12), for example by unscrewing it. The coupler (22) can then be discarded.

In an alternative sequence shown in FIG. 11, the method may detach (403) the injector (12) from the coupler (22) and then detach (404) the coupler (22) from the dispensing unit (20) and discard the coupler (22).

The drive unit (24) is then attached (405) to the dispensing unit (20). In the illustrated embodiment in FIG. 10E this is by sliding it into position. In other embodiments as described previously, this may be by vertically engaging the drive unit (24) onto the dispensing unit (20). The delivery device (10) is than applied (406) to the user that that the dispenser (28) pierces the user's skin.

Once connected as shown in FIG. 10F, the insulin delivery device (10) is then powered on, either automatically by sensing the connection of the drive unit (24) to the dispensing unit (20) or by means of user interaction such as through a switch on the drive unit (24) or a wireless instruction received from a user device. The device (10) then automatically runs through a series of system checks to ensure that it is ready without requiring any user intervention. Such system checks may include a power check, a check that there is medication fluid in the reservoir (30), and a check that it has communication with connected devices such as a patient monitor.

The drive unit (24) may be configured to automatically prime the dispensing unit (20) by actuating the drive mechanism to purge a known amount of air which may be present. Once primed, the insulin delivery device (10) is ready to begin delivering (407) insulin to the user at a final stage shown in FIG. 11.

The schedule for dosing the medication fluid to the user may be determined by instructions recorded on or determined by the control unit (64), which may be based upon information received from the user device and/or patient monitor. The information may include a type of medication fluid that will determine a dosing schedule. In one embodiment, the medication fluid is insulin and the patient monitor is a continuous glucose monitor (CGM). The control unit (64) may thus be configured to wirelessly pair with dedicated or proprietary CGM systems. Obtaining information from paired CGM systems enables the device to follow a predictive algorithm running onboard (or provided by an external system like the user device) rather than simply following a static schedule. The predictive algorithm may take into account information received from the CGM system including past, current and predicted future blood glucose and may employ machine learning to improve its accuracy over time as it obtains more data for the specific user. Depending upon the prediction algorithm, the device will then dose varying quantities of insulin to the user.

After a predetermined dosing time, which may for example be overnight, for one day or a portion of a day, the user simply removes (408) the adhesive patch (36) from their body using the non-adhesive tag (27). They then separate (409) the drive unit (24) from the dispensing unit (20) and place (410) the drive unit (24) on a charging station. The dispensing unit (20) itself is discarded. Provision for retracting and/or bending the dispenser (28) may also be made by means of a latching mechanism (not shown) that covers the dispenser to reduce the risk of an accidental prick.

The delivery device (10) may be used continuously through a period of constant application, intermittently through periods of application and non-application, or periodically through constant and/or intermittent use over multiple wear sessions.

To keep the cost of the device low it is intended to be used for a period of generally less than one day, such as 8 to 12 hours. This enables a smaller battery to be used than if the device were intended to operate for an extended period of time such as days or weeks. It is intended that the reservoir is only filled once so the device only has the volume of insulin in the reservoir (30) to dispense for a set period of time before a new dispensing unit (20) is required.

The delivery device (10) may work with any type of bolus insulin and any insulin pen type, with no additional medical prescription being required by the user. The dispensing unit (20) may be made as a low-cost device with a sleek, low profile, which is significantly less intrusive than existing insulin pumps. In this way, the insulin delivery device (10) provides a patch pump for delivery of insulin in a discrete manner, where the insulin has been provided by a user's preferred insulin pen.

Advantageously, the product delivers automation capabilities to insulin pen users that may be particularly advantageous at nighttime or at a time when a user does not wish to or is not able to regularly deliver medication. This may enable users to sleep through the night, wake up with more stable blood glucose, and increase their Time in Range (a measure of how long blood glucose levels are within a desired range).

Insulin pens are used primarily for controlling high blood sugar (by adding insulin); low blood sugar is dealt with by eating something. The device helps solve the high blood sugar problem, which is still a major issue at night. In some embodiments it can communicate with a wearable blood glucose meter to know when and how much insulin to dose.

An example use of the delivery device (10) is now described in the context of insulin delivery. Jane is a person with Type 1 diabetes who is taking insulin in multiple daily injections using a smart insulin pen. She has been able to control her glucose during the day, but in the early morning hours during her sleep she has consistently trended higher than target. After consulting with her physician, she uses the described delivery device (10) to better control hyperglycemia during the night. She receives a package with durable components that contains the drive unit (24), charging unit, and a USB cable. She places the drive unit (24) on the charger unit and connects the charger unit to a wall plug using the USB cable. Jane also receives a box with multiple disposable units that includes the dispensing unit (20) provided on a protective tray (19) and a coupler (22). The disposable units are packaged in a top and bottom packaging (15, 17) as shown in FIG. 4B.

In the evening, Jane peels open one of the packages and takes out the dispensing unit (20). She dials up 10 Units on her rapid acting insulin pen, inserts the insulin pen into the coupler (22) and fills the reservoir with 10 units of insulin. She removes the coupler (22) from the reservoir and discards it into a sharp's container.

Jane removes the drive unit (24) from the charger unit and snaps it over the dispensing unit (20) to connect the two pieces of the wearable patch. She peels the protective bottom packaging (17) off of the dispensing unit (20) and is now ready to apply the patch to her body.

Jane sleeps through the night and she checks her user device in the form of her smart phone and can see her CGM chart with hash marks at the times in which doses were given. Her glucose readings are within the target range. Satisfied, she removes the patch, discards it in a sharps container and continues with her day.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention.

Finally, throughout the specification and accompanying claims, unless the context requires otherwise, the word 'comprise' or variations such as 'comprises' or 'comprising' will be understood to imply the inclusion of a stated integer or group of integers but not the exclusion of any other integer or group of integers.

What is claimed is:

1. A medication fluid delivery device comprising:
   a dispensing unit having a dispenser for delivering a medication fluid to a user and a reservoir configured to be filled with a variable amount of the medication fluid received from a medication fluid injector; and
   a drive unit attachable to the dispensing unit, the drive unit including a control unit configured to control the drive unit and cause the medication fluid in the reservoir to be pumped through the dispenser;
   wherein the drive unit includes a registration mechanism configured to act with the dispensing unit to determine a state of the reservoir including an initial level of the medication fluid in the reservoir.

2. The medication fluid delivery device of claim 1, wherein the dispensing unit comprises a plunger moveable relative to the reservoir to apply a pressure to the medication fluid in the reservoir to pump it through the dispenser, and the drive unit comprises a plunger operating member configured to engage with the plunger and to be driven by a drive mechanism.

3. The medication fluid delivery device of claim 1, wherein the registration mechanism comprises a sensor of the state of the reservoir, and wherein the state of the reservoir is selected from the group consisting of: that the reservoir is present, that the reservoir is engaged but not ready, and a current level of the filled reservoir.

4. The medication fluid delivery device of claim 2, wherein the registration mechanism is integrated with the plunger operating member and is configured to detect a position of the plunger indicative of a state of the reservoir.

5. The medication fluid delivery of claim 2, wherein the registration mechanism is configured to determine a position for an initially filled state of the reservoir by moving the plunger operating member in a direction opposite to a direction for dispensing the medication fluid.

6. The medication fluid delivery device of claim 1, wherein the registration mechanism is configured to detect when the dispensing unit is attached to the drive unit.

7. The medication fluid delivery device of claim 2, wherein the control unit is configured to use the registration mechanism to determine a volume of the medication fluid in the reservoir based on the position of the plunger operating member.

8. The medication fluid delivery device of claim 2, wherein the registration mechanism is configured to determine a home position of the plunger operating member as a reference for an empty state of the reservoir and an initial register position of the plunger operating member for a filled state of the reservoir.

9. The medication fluid delivery device of claim 2, wherein the drive mechanism includes a stepper motor for controlling and measuring a linear movement of the plunger operating member and the control unit is configured to control the amount of delivery of the medication fluid by activation of steps of the stepper motor.

10. The medication fluid delivery device of claim 2, wherein the plunger operating member is configured to activate a sensor of a detached state when the dispensing unit is detached from the drive unit and of an operational state when the plunger operating member is engaged with the plunger ready for delivery of the medication fluid.

11. The medication fluid delivery device of claim 10, wherein the plunger operating member is configured to have a first orientation depending on and indicating when the drive unit is detached from the dispensing unit and a second orientation engaged with the plunger and indicating an operational state.

12. The medication fluid delivery device of claim 11, wherein the plunger operating member is configured to have a third orientation caused by the dispensing unit engaging with the drive unit and indicating a standby state ready for registering to result in the second orientation.

13. The medication fluid delivery device of claim 2, wherein the control unit is configured to automatically prime the plunger operating member by moving a predetermined priming distance in the plunger delivery direction to under-prime the medication fluid such that no medication fluid is delivered during the priming stage.

14. The medication fluid delivery device of claim 13, wherein the control unit is configured to determine that the dispensing unit is attached to the drive unit and control the plunger operating member to automatically prime the plunger operating member.

15. The medication fluid delivery device of claim 2, wherein the control unit is configured to reset the plunger operating member by moving the plunger operating member in the plunger delivery direction to a home position when it receives an indication that the drive unit is coupled to a charger unit.

16. The medication fluid delivery device of claim 1, wherein the drive unit comprises a plurality of electrical contacts which connect to a plurality of complementary electrical contacts of a recharging base station; and wherein the plurality of electrical contacts are configured to permit a power source to be recharged by the base station when the drive unit is disconnected from the dispensing unit.

17. The medication fluid delivery device of claim 1, wherein the control unit further comprises a wireless communication module configured for communication with a remote device for receiving information used by a dosing algorithm of the control unit to control the delivery of the medication fluid from the dispensing unit.

18. The medication fluid delivery device of claim 2, wherein the drive mechanism includes a stall detector configured to detect a motor stall due to an occlusion in the fluid delivery or a hard stop of movement of the plunger.

19. The medication fluid delivery device of claim 2, wherein the control unit is configured to initialize the plunger operating member by sensing that the dispensing unit is attached to the drive unit and controlling the drive mechanism to move in a first direction against the plunger delivery direction until the plunger operating member engages with an end of the plunger.

20. The medication fluid delivery device of claim 1, wherein the control unit is configured to generate status indications or alerts and transmit those indications or alerts to a user device and/or cause the indications or alerts to be displayed or indicated by the drive unit.

21. The medication fluid delivery device of claim 1, wherein the reservoir is configured to be filled from an auto-injector for automatically dispensing a pre-selected quantity of the medication fluid.

22. The medication fluid delivery device of claim 1, further comprising a coupler configured to releasably attach the dispensing unit to the medication fluid injector, wherein the coupler comprises a first interface configured to couple to the injector and a second interface configured to couple to the dispensing unit, wherein the second interface includes a sealing arrangement configured to block a fluid path to the dispenser during filling of the reservoir.

23. The medication fluid delivery device of claim 22, wherein the reservoir includes an inlet port configured to receive the medication fluid from the medication fluid injector and a second port configured to engage with the sealing arrangement.

24. The medication fluid delivery device of claim 22, wherein one of the first interface or the second interface has a stronger attachment arrangement than the other of the first interface or second interface for staged decoupling of the coupler after filling.

25. The medication fluid delivery device of claim 22, wherein the coupler provides a fluid passageway between the medication fluid injector and the reservoir and the coupler is discardable once the medication fluid injector is used to fill the reservoir.

26. The medication fluid delivery device of claim 1, wherein the dispensing unit comprises a housing in which the reservoir is held, and a planar adhesive patch disposed on one side of the housing, and wherein the dispenser is one or more needle or microneedle extending from an adhesive face of the adhesive patch opposite the housing, and wherein the planar adhesive patch includes a removal tab configured to aid removal from a user's skin.

27. The medication fluid delivery device of claim 26, wherein the drive unit and the dispensing unit are releasably attachable using a latch arrangement configured to disengage in a direction when a user holds the removal tab.

28. The medication fluid delivery device of claim 1, wherein the drive unit is releasably attachable to the dispensing unit by complementary formations on the drive unit and dispensing unit.

29. The medication fluid delivery device of claim 1, wherein the dispensing unit comprises a housing having an upstanding portion in which the reservoir and plunger are held including a rigid rib for engagement with a corresponding void of the drive unit.

* * * * *